United States Patent
Sako et al.

(12)

(10) Patent No.: US 6,436,441 B1
(45) Date of Patent: *Aug. 20, 2002

(54) HYDROGEL-FORMING SUSTAINED-RELEASE PREPARATION

(75) Inventors: Kazuhiro Sako; Hiroshi Nakashima; Toyohiro Sawada; Akira Okada; Muneo Fukui, all of Shizuoka (JP)

(73) Assignee: Yamanouchi Pharmaceutical Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/403,752

(22) PCT Filed: Sep. 10, 1993

(86) PCT No.: PCT/JP93/01297

§ 371 (c)(1),
(2), (4) Date: Mar. 20, 1995

(87) PCT Pub. No.: WO94/06414

PCT Pub. Date: Mar. 31, 1994

(30) Foreign Application Priority Data

Sep. 18, 1992 (JP) ............................................. 4-274979
Jun. 8, 1993 (JP) ............................................. 5-165263

(51) Int. Cl.[7] .......................... A61K 9/22; A61K 47/38; A61K 47/32; A61K 47/34
(52) U.S. Cl. ...................... 424/488; 424/487; 424/484; 424/468; 424/465
(58) Field of Search .......................... 424/486; 487/488, 487/457, 465, 468, 471, 475, 426, 428, 449, 484

(56) References Cited

U.S. PATENT DOCUMENTS

| 4,404,183 | A | * | 9/1983 | Kawata et al. | 424/501 |
|---|---|---|---|---|---|
| 4,764,378 | A | * | 8/1988 | Keith et al. | 424/486 |
| 4,806,337 | A | * | 2/1989 | Snipes et al. | 424/468 |
| 4,968,508 | A | | 11/1990 | Oren et al. | |
| 5,273,758 | A | * | 12/1993 | Royce | 424/486 |
| 5,650,170 | A | * | 7/1997 | Wright et al. | |
| 5,681,584 | A | * | 10/1997 | Savastino et al. | |

FOREIGN PATENT DOCUMENTS

| DE | A1 42 26 753 | 2/1994 |
|---|---|---|
| EP | 0067671 | 12/1982 |
| JP | 40-2053 | 2/1965 |
| JP | 56-49314 | 5/1981 |
| WO | WO 91/19481 | 12/1991 |
| WO | WO9401483 | 1/1994 |

OTHER PUBLICATIONS

Partial copy of Handbook of Pharmaceutical Excipients, (Mar. 30, 1989).
Product Safety Data Sheets for Kollidon VA64 (Oct. 18, 1993).
"Poly (Ethylene Oxide)", Handbook of water–soluble gums and resins, Union Carbide, 4/90.
J. Devane et al, "New Developments in Sustained–Release Antihypertensive Therapy: Formulation and Pharmacokinetic Considerations," Am J. Cardiology, vol. 69, Apr. 30, 1992.

* cited by examiner

Primary Examiner—Edward J. Webman
(74) Attorney, Agent, or Firm—Sughrue, Mion, Zinn Macpeack & Seas, PLLC

(57) ABSTRACT

The invention provides a hydrogel-type sustained-release preparation comprising (1) at least one drug, (2) an additive which insures a penetration of water into the core of the preparation and (3) a hydrogel-forming polymer, wherein said preparation is capable of undergoing substantially complete gelation during its stay in the upper digestive tract such as stomach and small intestine and is capable of releasing the drug in the lower digestive tract including colon.

By the preparation of the invention, the drug is efficiently released and absorbed even in the colon so that a steady and sustained release effect can be achieved.

30 Claims, 11 Drawing Sheets

HYDROGEL-FORMING SUSTAINED-RELEASE PREPARATION

TECHNICAL FIELD

The present invention relates to a sustained-release preparation capable of releasing a drug for a prolonged period of time. More particularly, the invention relates to a hydrogel-type sustained-release preparation capable of satisfactorily releasing a drug not only in the upper digestive tract but also in the lower digestive tract, particularly in the colon.

BACKGROUND ART

A variety of hydrogel-type preparations have heretofore been proposed for realizing sustained release of drugs. For example, JP-A-62-120315 discloses a preparation obtained by compression-molding a drug, a hydrogel-forming water-soluble polymer and an enteric coating base (the term "JP-A"as used herein means an "unexamined published Japanese patent application"). JP-A-63-215620 discloses a hydrogel-type preparation which comprises a core comprising a drug and a water-soluble polymer and an outer layer comprising a water-soluble polymer as a base. JP-B-40-2053 discloses a sustained-release preparation comprising a mixture of a drug and a high polymer of ethylene oxide and, as an optional component, a hydrophilic substance (the term "JP-B" as used herein means an "examined Japanese patent publication").

However, all of these preparations are designed to release a drug continuously while the administered preparation is still retained in the upper digestive tract, typically in the stomach and small intestine, and are not intended to provide for a release of the drug in the lower digestive tract, typically in the colon, where little water is available. Thus, for any sustained-release preparation designed to release a drug for absorption during its descent down in the digestive tract, the extent of drug release and absorption in the upper digestive tract has a major influence on the bioavailability of the drug. However, it is generally believed that the release of the drug in the colon can hardly be expected because of the paucity of water and the influence of spodogenous contents etc. and actually, little research has been undertaken on drug release in the colon (Pharm. Tech. Japan 8 (1), (1992), 41).

Furthermore, the biological half-life of a drug per se is also an important factor in the design of sustained-release preparations. It has been generally considered difficult to design a preparation providing for dramatic sustained release for a drug having a short half-life period (The Pharmaceuticals Monthly 25 (11), (1983), 29).

DISCLOSURE OF INVENTION

As a result of extensive studies on the sustained-release of a drug, the inventors of the present invention discovered that the release of a drug in the colon, which is low in water content, can be achieved by providing a preparation adapted to absorb water into its core to undergo substantially complete gelation during its stay in the upper digestive tract such as the stomach and small intestine, and then move in the form of the gel down to the lower digestive tract. The present invention was achieved based on the above finding.

Thus, the present invention relates to a hydrogel-type sustained-release preparation comprising (1) at least one drug, (2) an additive providing for a penetration of water into the core of the preparation, and (3) a hydrogel-forming polymer, which preparation undergoes a substantially complete gelation during its stay in the upper digestive tract such as the stomach and small intestine and is capable of releasing a drug in the colon.

The term "substantially complete gelation" of the preparation as used in this specification refers to the state in which not less than about 70%, preferably not less than about 80%, of the preparation is gelled.

Since even the colon can be utilized as a site of absorption, the sustained-release preparation of the present invention prolongs the absorption period of the drug to a remarkable extent and, hence, insures a steady blood level of the drug. Thus, the preparation of the present invention absorbs water during its stay in the upper digestive tract to undergo a substantially complete gelation and then moves down into the lower digestive tract with its surface being constantly eroded, and maintains drug release by further erosion in the lower digestive tract, with the result that a sustained and sufficient absorption of the drug is achieved even in the colon where little water is available.

The sustained-release preparation of the present invention is described in further detail hereinafter.

The drug or drugs which can be used in the preparation according to the present invention are not particularly limited in kind, provided that they are used for sustained-release system.

Thus, representative examples of the drugs include antiinflammatory, antipyretic, anticonvulsant and/or analgesic agents such as indomethacin, diclofenac, diclofenac Na, codeine, ibuprofen, phenylbutazone, oxyphenbutazone, mepirizol, aspirin, ethenzamide, acetaminophen, aminopyrine, phenacetin, scopolamine butylbromide, morphine, etomidoline, pentazocine, fenoprofen calcium, etc; tuberculostats such as isoniazid, ethambutol hydrochloride, etc.; cardiocirculatory system drugs such as isosorbide dinitrate, nitroglycerin, nifedipine, barnidipine hydrochloride, nicardipine hydrochloride, dipyridamole, amrinone, indenolol hydrochloride, hydralazine hydrochloride, methyldopa, furosemide, spironolactone, guanethidine nitrate, reserpine, amosulalol hydrochloride, etc.; antipsychotic agents such as chlorpromazine hydrochloride, amitriptyline hydrochloride, nemonapride, haloperidol, moperone hydrochloride, perphenazine, diazepam, lorazepam, chlordiazepoxide, etc.; antihistaminic agents such as chlorpheniramine maleate, diphenhydramine hydrochloride, etc.; vitamins such as thiamine nitrate, tocopherol acetate, cycothiamine, pyridoxal phosphate, cobamamide, ascorbic acid, nicotinamide, etc.; antigout agents such as allopurinol, colchicine, probenecid, etc.; hypnotic sedatives such as amobarbital, bromovalerylurea, midazolam, chloral hydrate, etc.; antineoplastic agents such as fluorouracil, carmofur, aclarubicin hydrochloride, cyclophosphamide, thiotepa, etc.; anticongestants such as phenylpropanolamine, ephedrine, etc.; antidiabetics such as acetohexamide, insulin, tolbutamide, etc.; diuretics such as hydrochlorothiazide, polythiazide, triamterene, etc.; bronchodilators such as aminophylline, formoterol fumarate, theophylline, etc; antitussives such as codeine phosphate, noscapine, dimemorfan phosphate, dextromethorphan, etc; antiarrhythmic agents such as quinidine nitrate, digitoxin, propafenone hydrochloride, procainamide, etc.; surface anesthetics such as ethyl aminobenzoate, lidocaine, dibucaine hydrochloride, etc.; antiepileptics such as phenytoin, ethosuximide, primidone, etc.; synthetic adrenocortical steroids such as hydrocortisone, prednisolone, triamcinolone, betamethasone, etc.; digestive system drugs such as famotidine, ranitidine hydrochloride, cimetidine, sucralfate, sulpiride, teprenone, plaunotol, etc.; central nervous system drugs such as indeloxazine, idebenone, tiapride hydrochloride, bifemeline hydrochloride, calcium hopantenate, etc.; hyperlipemia treating agents such as pravastatin sodium etc.; and antibiotics such as ampicillin phthalidyl hydrochloride, cefotetan, josamycin and so on. A typical drug among the above drugs is nicardipine hydrochloride. Drugs having short biological half-lives can also be utilized. The amount of the drug may be any of pharmaceutically effective amount, but is usually below 85 weight %, and preferably below 80 weight % based on the total weight of the preparation.

In order that these drugs may be readily absorbed in the colon which is low in water content, it is preferable to improve their solubilities in advance. Known techniques for improving the solubility of a drug which can be applied to hydrogel preparation can be employed. Among such techniques (solubilizing treatment) can be mentioned the method comprising adding a surfactant (e.g. polyoxyethylene-hydrogenated castor oils, polyoxy-ethylene-sorbitan higher fatty acid esters, polyoxyethylene polyoxypropylene glycols, sucrose fatty acid esters, etc.) and the method comprising preparing a solid dispersion of the drug and a solubilizer such as a polymer (e.g., a water-soluble polymer such as hydroxypropylmethylcellulose (HPMC), polyvinylpyrrolidone (PVP), polyethylene glycol (PEG), etc. or an enteric polymer such as carboxymethylethylcellulose (CMEC), hydroxypropylmethylcellulose phthalate (HPMCP), methyl methacrylate-methacrylic acid copolymer (Eudragit L and S; the trade name of Rhom & Haas Co.), etc.). When the drug is a basic substance, the method comprising adding an. organic acid such as citric acid, tartaric acid or the like can be employed. If necessary, the method involving the formation of a soluble salt or the method comprising forming a clathrate using cyclodextrin or the like can also be employed. These procedures for solubilization can be modified as necessary according to the particular drug.

["Recent Manufacturing Pharmacy Technique and its Application I", Isamu Utsumi et al., *Medicinal Journal*, 157–159 (1983); and "Pharmacy Monograph No. 1, Bioavailability", Tsuneji Nagai et al., Softscience Co., 78–82 (1988)]

Among these methods, the method comprising preparing a solid dispersion of the drug and a solubilizer is particularly preferred (cf. JP-A-56-49314 and French Patent 2460667).

The additive for allowing water to penetrate into the core of the preparation according to the present invention (this additive for insuring a penetration of water into the preparation core will hereinafter be referred to as "hydrophilic base") is such that the amount of water required to dissolve 1 g of the hydrophilic base is not more than 5 ml and preferably not more than 4 ml at the temperature of 20±5° C. The higher the solubility of the hydrophilic base in water, the more effective is the base in allowing water into the core of the preparation. The hydrophilic base includes, inter alia, highly hydrophilic polymers such as polyethylene glycol (PEG; e.g. PEG400, PEG1500, PEG4000, PEG6000 and PEG20000, produced by Nippon Oils and Fats Co.) and polyvinylpyrrolidone (PVP; e.g. PVP K30, the trade name of BASF), sugar alcohols such as D-sorbitol, xylitol, etc., sugars such as sucrose, anhydrous maltose, D-fructose, dextran (e.g. dextran 40), glucose, etc., surfactants such as polyoxyethylene-hydrogenated castor oil (HCO; e.g. Cremophor RH40 produced by BASF, HCO-40 and HCO-60 produced by Nikko Chemicals Co.), polyoxyethylene-polyoxypropylene glycol (e.g. Pluronic F68 produced by Asahi Denka Kogyo K.K.), polyoxyethylene-sorbitan high molecular fatty acid ester (Tween; e.g. Tween 80 produced by Kanto Kagaku K.K.), etc.; salts such as sodium chloride, magnesium chloride, etc.; organic acids such as citric acid, tartaric acid, etc.; amino acids such as glycine, β-alanine, lysine hydrochloride, etc.; and amino sugars such as meglumine.

Preferred ones are PEG6000, PVP, D-sorbitol, etc.

The proportion of such hydrophilic base depends on the characteristics of the drug (solubility, therapeutic efficacy, etc.) and content of the drug, solubility of the hydrophilic base itself, characteristics of the hydrogel-forming polymer used, the patient's condition at the time of administration and other factors. However, the proportion may preferably be a sufficient level to achieve a substantially complete gelation during the stay of the preparation in the upper digestive tract. The preparation stays in the upper digestive tract in a different period depending on the species and the individual but in about 2 hours after administration in the case of dogs and in about 4 to 5 hours after administration in the case of human (*Br. J. clin. Pharmac,* (1988) 26, 435–443). For administration to human, the proportion may preferably be a sufficient level to achieve a substantially complete gelation in about 4 to 5 hours after administration. The proportion of the hydrophilic base is, therefore, generally about 5–80% by weight and preferably about 5–60% by weight based on the total weight of the preparation.

When the content of the hydrophilic base is too small, the necessary gelation into the core of the preparation does not proceed so that the release of the drug in the colon becomes insufficient. On the other hand, when the content of the hydrophilic base is excessive, the gelation proceeds in a shorter time but the resulting gel becomes so fragile that the release of the drug is too fast, thus failing to insure a sufficient sustained release. Moreover, because the amount of the base is large, the product becomes bulky.

The hydrogel-forming polymer mentioned above should have the physical characteristics, inclusive of viscosity in the gelled state, which permit the preparation of the present invention to retain its shape more or less during its travel down to the lower digestive tract, namely the colon, by withstanding the contractile forces of the digestive tract associated with the digestion of food.

The hydrogel-forming polymer which can be used in the preparation of the present invention is preferably a polymer showing a high viscosity on gelation. For example, a polymer showing a viscosity of not less than 1000 cps in 1% aqueous solution (at 25° C.) is particularly preferred.

The properties of the polymer depend on its molecular weight. The hydrogel-forming polymer which can be used in the present invention is preferably a substance of comparatively high molecular weight, viz. a polymer having an average molecular weight of not less than $2 \times 10^6$ and more preferably not less than $4 \times 10^6$.

Among such polymers are polyethylene oxide (PEO) having a molecular weight of not less than $2 \times 10^6$ [e.g., Polyox WSR-303 (average mol. wt.: $7 \times 10^6$; viscosity: 7500–10000 cps, 1% in $H_2O$, 25° C.), Poly WSR Coagulant (average mol. wt.: $5 \times 10^6$; viscosity: 5500–7500 cps, under the same condition above), Polyox WSR-301 (average mol. wt.: $4 \times 10^6$; viscosity: 1650–5500 cps, under the same condition above), Polyox WSR-N-60K (average mol. wt.: $2 \times 10^6$; viscosity: 2000–4000 cps, 2% in $H_2O$, 25° C.), all of which are trade names of Union Carbide Co.]; hydroxypropylmethylcellulose (HPMC) [e.g., Metolose 90SH100000 (viscosity: 4100–5600 cps., 1%; in $H_2O$, 20° C.), Metolose 90SH50000 (viscosity: 2900–3900 cps, under the same condition above), Metolose 90SH30000 (viscosity: 25000–35000 cps, 2% in $H_2O$, 20° C.), all of which are trade names of Shin-Etsu Chemicals Co.]; sodium carboxymethylcellulose (CMC-Na) [e.g., Sanlose F-150MC (average mol. wt.: $2 \times 10^5$; viscosity: 1200–1800 cps, 1% in $H_2O$, 25° C.), Sanlose F-1000MC (average mol. wt.: $42 \times 10^4$; viscosity: 8000–12000 cps, under the same condition above), Sanlose F-300MC (average mol. wt.: $3 \times 10^5$; viscosity: 2500–3000 cps, under the same condition above), all of which are trade names of Nippon Seishi Co., Ltd.]; hydroxyethylcellulose (HEC) [e.g., HEC Daicel SE850 (average mol. wt.: $148 \times 10^4$; viscosity: 2400–3000 cps, 1% in $H_2O$, 25° C.), HEC Daicel SE900 (average mol. wt.: $156 \times 10^4$; viscosity: 4000–5000 cps, under the same condition above), all of which are trade names of Daicel Chemical Industries]; carboxyvinyl polymers [e.g., Carbopol 940 (average mol. wt.: ca. $25 \times 10^5$; B.F. Goodrich Chemical Co.) and so on.

The preferred is a PEO having an average molecular weight of not less than $2 \times 10^6$. Where a continuous release of the drug over a long time, for example more than 12 hours, is required, a polymer having a higher molecular weight, preferably an average molecular weight of not less than $4 \times 10^6$, or a higher viscosity, preferably a viscosity of not less than 3000 cps at a concentration of 1% in water at 25° C., is preferable.

The above hydrogel-forming polymer may be used singly, or two or more kind(s) of the above hydrogel-forning polymers in mixture may be used. Or, the mixture of two or more kinds of any polymers, which mixture has characteristics suitable for the present invention, may be suitably used for the present invention.

In order to insure a release of the drug in the human colon, it is necessary that a portion of the preparation having undergone gelation still remain in the colon even as late as at least 6–8 hours, preferably at least 12 hours, after administration.

In order to provide a hydrogel-type preparation having such properties, although it depends on the volume of the preparation, the kind of polymer and the properties and amount of the drug and of the additive for insuring a penetration of water into the preparation core, it is generally preferable that the preparation contains 10–95 weight % (preferably, 15–90 weight %) of the hydrogel-forming polymer based upon the preparation weighing less than 600 mg, and one preparation contains not less than 70 mg per preparation and preferably not less than 100 mg per preparation of the hydrogel-forming polymer. If the amount of this polymer is less than the above-mentioned level, the preparation will not tolerate erosion in the digestive tract for a sufficiently long time and a sufficient sustained release may not be achieved.

Regarding the types and proportions of the hydrophilic base and hydrogel-forming polymer (the latter is hereinafter referred to as hydrogel-forming base), their usefulness has been established by the following experiments.

Experimental Example

Types and Proportions of Hydrophilic Base and Hydrogel-Forming Base (1) The Time Course of Gelation Velocity of the Hydrogel-type Sustained-release Preparation According to the Present Invention Sample 100 parts by weight of hydrogel-forming base Polyox WSR-303 (referred to as POLYOX303 hereinafter) blended with 150 parts by weight of hydrophilic base PEG6000 was mixed in a mortar. The mixed composition was compression-molded using an oil press at a compression pressure of 1 ton/punch to provide tablets each measuring 8.0 mm in diameter and weighing 200 mg.

Gelation Test

Using The Pharmacopeia of Japan XII (referred to "JP" hereinafter) Disintegration Test Fluid 2, a gelation test was carried out by JP Dissolution Test Method 2 (paddle method) at a paddle speed of 25 rpm. Sample tablets were taken out at predetermined intervals, the gel layer was removed and the diameter (D obs) of the portion not forming a gel was measured. From this D obs value, the gelation index (G) was calculated (Table 1, FIG. 1 and Equation 1).

The "gelation index" as used herein represents the percentage of the portion of the tablet which has undergone gelation. The method of calculating the gelation index is not particularly limited but the following calculation method may be mentioned as an example.

Thus, the test tablet is moistened for a predetermined time, the volume (or weight) of the portion not forming a gel is then measured and the result is subtracted from the volume (or weight) of the tablet before the beginning of the test.

To be specific, the gel layer of the tablet moistened for a predetermined time is removed, the diameter (or thickness) of the portion not forming a gel is then measured and the gelation index is calculated by means of Equation 1. The gelation index may also be calculated by means of Equation 2 given hereinafter.

As an alternative which takes advantage of the difference in strength between the gel layer and non-gel portion, the diameter (or thickness) under a predetermined pressure is assumed to be the diameter (or thickness) of the portion not forming a gel and the gelation index is calculated from Equation 1.

TABLE 1

Results of Gelation Test

| Testing Time (h) | D obs (mm) | G (%) |
|---|---|---|
| 0 | 8.0 ± 0.0 | 0 |
| 0.5 | 6.8 ± 0.03 | 37.9 ± 0.7 |
| 1.0 | 5.8 ± 0.2 | 61.1 ± 1.8 |
| 2.0 | 4.0 ± 0.05 | 87.9 ± 0.4 |
| 3.0 | 2.0 ± 0.0 | 98.4 ± 0.0 |
| 4.0 | 0.0 | 100 |
| 5.0 | 0.0 | 100 |

(n = 3, Mean ± S.E.)

Equation 1

$$\text{Gelation Index } (G, \%) = \left(1 - \frac{(D \ obs)^3}{(D \ ini)^3}\right) \times 100$$

$D\ obs$: The diameter of the portion not gelled after initiation of the test $D\ ini$: The diameter of the preparation before initiation of test Results The hydrogel tablet containing PEG6000 as a hydrophilic base underwent gelation with its core diameter diminishing progressively at a substantially constant rate. Two hours after the initiation of the test, the hydrogel tablet substantially went through gelation (not less than 80%).

(2) Content of Hydrophilic Base

Samples

One-hundred parts by weight of the hydrogel-forming base POLYOX303 blended with a varying proportion, from 0 to 150 parts by weight, of the hydrophilic base PEG6000 was mixed in a mortar and compression-molded using an oil press at a compression pressure of 1 ton/punch to provide tablets each measuring 8.0 mm in diameter and weighing 200 mg.

Gelation Test

Using JP Disintegration Test Fluid No. 2, the gelation test was performed by JP Dissolution Test Method 2 (paddle method) at a paddle speed of 25 rpm. The tablets were taken out at predetermined intervals, the gel layer was stripped off and the diameter (D obs) of the portion not forming a gel was measured. From the D obs value, the gelation index (G) was calculated (Table 2 and FIG. 2).

TABLE 2

Results of Gelation Test

| Blending Ratio | G (%) | |
|---|---|---|
| POLYOX303:PEG6000 | 2 h | 4 h |
| 100:0 | 29.7 ± 2.9 | 50.5 ± 1.4 |
| 100:5 | 44.2 ± 5.2 | 78.0 ± 2.1 |
| 100:10 | 52.3 ± 2.5 | 83.9 ± 0.5 |
| 100:15 | 84.6 ± 0.5 | 91.2 ± 2.0 |
| 100:25 | 84.6 ± 0.6 | N.T. |
| 100:50 | 85.2 ± 0.6 | N.T. |
| 100:100 | 87.1 ± 0.2 | N.T. |
| 100:150 | 87.9 ± 0.4 | 100.0 ± 0.0 |

N.T.: Not Tested
(n = 3, Mean ± S.E.)

Results

It was found that the inclusion of 15 parts by weight (13.0% of tablet weight) of the hydrophilic base PEG6000 resulted in not less than 80% gelation in 2 hours. It was also found that the inclusion of 10 parts by weight (9.% of tablet weight) of the hydrophilic base PEG6000 resulted in not less than 80% gelation in 4 hours.

(3) Screening of Hydrophilic Bases

Samples

One-hundred parts by weight of the hydrogel-forming base POLYOX303 blended with 100 parts by weight of each test hydrophilic base was mixed in a mortar and compression-molded using an oil press at a compression pressure of 1 ton/punch to provide tablets each measuring 8.0 mm in diameter and weighing 200 mg.

Gelation Test

Using JP Disintegration Test Fluid No. 2, the gelation test was performed by JP Dissolution Test Method 2 (paddle method) at a paddle speed of 25 rpm. The tablets were taken out at 2 hours after initiation of the test and the gel layer was stripped off and the diameter (D obs) of the portion not forming a gel was measured. From the D obs value, the gelation index (G) was calculated (Table 3 and FIG. 3).

TABLE 3

Influence of Solubility of Various Additives on Gelation Index

| Additive | Solubility** | G (%) |
|---|---|---|
| No additive | | 29.7 ± 2.9 |
| Lactose | 8 ml | 24.4 ± 1.9 |
| D-Mannitol | 6 ml | 26.8 ± 1.9 |
| Inositol | 6 ml | 42.0 ± 1.5 |
| Glycine | 4 ml | 80.9 ± 0.7 |
| PEG20000 | 4 ml | 86.2 ± 0.3 |
| Pluronic F68* | 4 ml | 95.1 ± 0.4 |
| PVP K30 | 2 ml | 82.2 ± 2.5 |
| Dextran 40 | 2 ml | 85.9 ± 1.0 |
| Meglumine | 2 ml | 93.4 ± 0.8 |
| Dextrose Anhydrous | 2 ml | 94.2 ± 1.5 |
| Lysine-HCl | 2 ml | 95.1 ± 1.3 |
| β-Alanine | 2 ml | 99.3 ± 0.2 |
| PEG6000 | 1 ml | 87.1 ± 0.2 |
| Citric acid | 1 ml | 93.2 ± 0.3 |
| Maltose Anhydrous | 1 ml | 93.7 ± 0.7 |
| Xylitol | 1 ml | 94.0 ± 1.4 |
| Sucrose | 1 ml | 94.2 ± 1.1 |
| D-Sorbitol | 1 ml | 97.0 ± 0.4 |
| D-Fructose | 1 ml | 100 |

*Polyoxyethylene[160]polyoxypropylene[30]glycol
(n = 3, Mean ± S.E.)
**Volume of water required for dissolving 1 gram measured in accordance with the method for solubility measurement in JP (25 ± 5° C.)

Results

When D-mannitol and lactose, which require more than 6 ml of water and 8 ml of water for dissolution of 1 g, were respectively added, the systems showed gelation indices comparable to the index of the system using POLYOX303 alone, indicating that these additives are less effective in causing gelation to proceed into the core of the tablet.

It was found that as the hydrophilic base providing for not less than 80% gelation in 2 hours, highly soluble bases (which require not more than 5 ml, preferably not more than 4 ml, of water for dissolution of 1 gram) such as glycine, PVP K30, PEG6000 and D-sorbitol are suitable.

(4) Studies on Hydrogel-Forming Base

Using acetaminophen and nicardipine hydrochloride (Pd) as model drugs, the proportion and molecular weight of a hydrogel-forming base which are necessary for the sustained-release preparation were investigated.

I. Study of Optimum Proportion

The relationship between the proportion of a hydrogel-forming base and the pattern of dissolution was investigated.

1. Acetaminophen

TABLE 4

| Formula (mg) | | | | | |
|---|---|---|---|---|---|
| Acetaminophen | 50 | 50 | 50 | 50 | 50 |
| PEG6000 | 50 | 50 | 50 | 50 | 50 |
| POLYOX303 | 40 | 50 | 100 | 150 | 300 |
| Weight (mg) | 140 | 150 | 200 | 250 | 400 |
| Diameter (mm) | 6.5 | 7.0 | 8.0 | 8.5 | 9.5 |

The components mentioned in Table 4 in the indicated proportions were mixed in a mortar, respectively, and each composition was compression-molded using an oil press at a compression pressure of 1 ton/punch to provide tablets (each containing 50 mg of acetaminophen).

2. Nicardipine Hydrochloride (Pd)

In a mixture of water and methanol (1:9) were dissolved 1 part by weight of Pd, 0.2 part by weight of HCO-60 and 0.4 part by weight of hydroxypropylmethylcellulose (TC- 5E, produced by Shin-Etsu Chemical Co.) and the solution was spray-dried using a spray dryer to provide Spray-dried Product 1.

TABLE 5

| Formula (mg) | | | | | | | |
|---|---|---|---|---|---|---|---|
| Spray-Dried Product | 128 | 128 | 128 | 128 | 128 | 128 | 128 |
| PEG6000 | 32 | 32 | 32 | 32 | 32 | 32 | 32 |
| POLYOX303 | 64 | 96 | 120 | 160 | 200 | 240 | 320 |
| Weight (mg) | 224 | 256 | 280 | 320 | 360 | 400 | 460 |
| Diameter (mm) | 8.5 | 8.5 | 8.5 | 9.0 | 9.0 | 9.5 | 10.0 |

The component materials mentioned in Table 5 in the indicated proportions were respectively mixed in a mortar ind each composition was compression-molded using an oil press at a compression pressure of 1 ton/punch to provide tablets (each containing 80 mg of Pd).

Dissolution Test

Using JP Disintegration Test Fluid 1 or 2, the dissolution test was carried out by JP Dissolution Test Method 2 (paddle method) using the acetaminophen and nicardipine hydrochloride (Pd) tablets as models. Sampling was performed at predetermined intervals and the amount of the drug in each sample was determined by the UV method (FIGS. 4 and 5).

Results

It was found that the rate of dissolution could be controlled by varying the proportion of the hydrogel-forming base POLYOX303. It was also found that when 50 mg of acetaminophen was used as the principal agent and not less than 100 mg (50% of tablet weight) of POLYOX303 was added, a sustained release of the drug lasting for not less than 12 hours was realized even under vigorous agitation (paddle speed 200 rpm, pH 6.8). Similarly, when 80 mg of Pd was used as the principal agent, the inclusion of not less than 96 mg (37.5% of tablet weight) of POLYOX303 insured a sustained release lasting for not less than 12 hours even under vigorous agitation (paddle speed 200 rpm, pH 1.2).

The optimum proportion of the hydrogel-forming base depends on the types and amounts of the drug and hydrophilic base and the desired dissolution rate, among other factors, but it was found that the larger was the proportion of the hydrogel-forming base, the greater was the sustainment of release. It was also found that when a sustained release lasting for not less than 12 hours is desired, it is necessary to include not less than about 70 mg, preferably not less than 100 mg, of the hydrogel-forming base per tablet.

II. Study of Relationship between Molecular Weight of Hydrogel-Forming Base and Duration of Release
  1. Acetaminophen

TABLE 6

| Formula (Parts by Weight) | |
|---|---|
| Acetaminophen | 50 |
| PEG6000 | 50 |
| Polyethylene Oxide (PEO) | 250 |

As the polyethylene oxide (PEO), those species having average molecular weights of $9 \times 10^5$, $1 \times 10^6$, $2 \times 10^6$, $4 \times 10^6$, $5 \times 10^6$ and $7 \times 10^6$ were used. In each case, the component materials were mixed in a mortar and compression-molded using an oil press at a compression pressure of 1 ton/punch to provide tablets each measuring 9.0 mm in diameter and weighing 350 mg.

2. Nicardipine Hydrochloride (Pd)

In a mixture of water and methanol (1:9) were dissolved 1 part by weight of Pd, 0.4 part by weight of HCO-40 and 0.8 part by weight of hydroxypropylmethylcellulose (TC-5E, produced by Shin-Etsu Chemical Co.) and the solution was spray-dried using a spray dryer to provide Spray-dried Product 2.

TABLE 7

| Tablet Formula (Parts by Weight) | |
|---|---|
| Spray-Dried Product 2 | 178 |
| PEG6000 | 48 |
| Polyethylene Oxide (PEO) | 344 |

As the polyethylene oxide (PEO), those species having average molecular weights of $9 \times 10^5$, $1 \times 10^6$, $2 \times 10^6$, $4 \times 10^6$, $5 \times 10^6$ and $7 \times 10^6$ were used. In each case, the component materials were mixed in a mortar and compression-molded using an oil press at a compression pressure of 1 ton/punch to provide tablets each measuring 11.0 mm in diameter and weighing 568 mg (containing 80 mg of Pd).

Release Test

The acetaminophen- and nicardipine-containing preparations were tested in the same manner as the dissolution test carried out in I. Study of the Optimal Proportion (FIGS. 6 and 7).

Results

The rate of dissolution varied with different average molecular weights of hydrogel-forming base polyethylene oxide (PEO). When 50 mg of acetaminophen was used as the principal agent, the use of PEO with an average molecular weight of not less than $4 \times 10^6$ resulted in a sustained release lasting for not less than 12 hours under vigorous agitation (paddle speed 200 rpm, pH 6.8).

Similarly, when 80 mg of Pd was used as the principal agent, the use of PEO with an average molecular weight of not less than $2 \times 10^6$ enabled a sustained release lasting for not less than 12 hours.

(5) Verification of In Vivo Gelation

Samples

The hydrogel-forming base (POLYOX303) and the hydrophilic base (PEG6000, PVP K30, or D-sorbitol) in the ratios indicated below were respectively mixed in a mortar and each mixture was compression-molded using an oil press at a compression pressure of 1 ton/punch to provide tablets each measuring 8.0 mm in diameter and weighing 200 mg.

POLYOX303:PEG6000=100:10, 25, 50, 100

POLYOX303:PVP K30=100:10, 25, 100

POLYOX303:D-sorbitol=100:10, 25, 100

Autopsy Test in Dogs

Male beagle dogs (Dogs A and B) fasted for about 20 hours were respectively dosed orally with each test preparation, together with 30 ml of water. Two hours later, the animals were anesthetized with pentobarbital Na and, after bleeding, the abdomen was opened. The tablet was recovered from the digestive tract and the D obs value was determined. From this D obs value, the gelation index (G) was calculated (Table 8).

TABLE 8

Autopsy Test Data in Dogs

| Dog | Sample Administered (POLYOX303 100:) | | Position of Recovery | Autopsy Data | | In Vitro |
|---|---|---|---|---|---|---|
| | | | | D obs (mm) | G (%) | G (%) |
| A | PEG6000 | 10 | Colon | 6.8 | 38.6 | 52.3 |
| | PEG6000 | 25 | Colon | 2.8 | 95.7 | 84.6 |
| | PEG6000 | 50 | Colon | N.D. | 100 | 85.2 |
| | PEG6000 | 100 | Colon | N.D. | 100 | 87.1 |
| | PVP K30 | 100 | Colon | N.D. | 100 | 82.2 |
| | D-Sorbitol | 100 | Colon | N.D. | 100 | 97.0 |
| B | PEG6000 | 10 | Stomach | 3.2 | 93.6 | 52.3 |
| | PEG6000 | 25 | Stomach | 2.9 | 95.2 | 84.6 |
| | PVP K30 | 10 | Stomach | 2.5 | 96.9 | — |
| | PVP K30 | 25 | Stomach | 2.9 | 95.2 | — |
| | D-Sorbitol | 10 | Stomach | 2.3 | 97.6 | — |
| | D-Sorbitol | 25 | Stomach | 2.9 | 95.2 | — |

N.D.: Not Detected

Results

In Dog A, the tablets had already been transported to the colon by 2 hours after administration and the upper digestive tract residence time was less than 2 hours. In contrast, all the tablets except the one containing 10 parts of PEG6000 had already undergone not less than 80% gelation, generally in agreement with in vitro data.

In Dog B, the tablets remained in the stomach at 2 hours after administration and all the tablets had undergone more than 80% gelation.

The above results indicated that hydrogel tablets containing a hydrophilic base providing for not less than 80% gelation in vitro (PVP K30, PEG6000 and D-sorbitol) in appropriate amounts are ready to gel due to penetration of water into the tablet core even in vivo.

If necessary, the preparation of the present invention may include appropriate other pharmaceutically acceptable additives such as vehicles (e.g., lactose, mannitol, potato starch, wheat starch, rice starch, corn starch, and crystalline cellulose), binders (e.g., hydroxylpropylmethylcellulose, hydroxypropylcellulose, methylcellulose, and gum arabic), swelling agents (e.g., carboxymethylcellulose, carboxymethylcellulose calcium, and cross-linking carboxymethylcellulose sodium), lubricants (e.g., stearic acid, calcium stearate, magnesium stearate, talc, magnesium meta-silicate aluminate, calcium hydrogen phosphate, and anhydrous calcium hydrogen phosphate), fluidizers (e.g., hydrous silica, light anhydrous silicic acid, and dried aluminum hydroxide gel), colorants (e.g., yellow iron sesquioxide and iron sesquioxide), surfactants (e.g., sodium lauryl sulfate, sucrose fatty acid ester), coating agents (e.g., zein, hydroxypropylmethylcellulose, and hydroxypropylcellulose), aromas (e.g., l-menthol, peppermint oil, and fennel oil), preservatives (e.g., sodium sorbate, potassium sorbate, methyl p-benzoate, and ethyl p-benzoate), etc.

The preparation of the present invention is a solid preparation having a certain shape and hydrogel-forming ability, and can be manufactured by the conventional processes utilized for the production of hydrogel preparations. Typical processes are the compression tabletting comprising blending the drug, hydrophilic base and hydrogel-forming polymer, if necessary with the addition of other additives, and compression-molding the resulting composition; the capsule compression filling; the extrusion molding comprising fusing a mixture and setting the fused mixture; and the injection molding; etc. Thereafter, any coating treatment such as sugar coating and film coating may be applied or filing into capsules may be carried out.

Solubilization, if performed, of the drug for use in the preparation of the invention can be carried out prior to the above-described manufacturing process. The hydrophilic base according to the present invention may double as said solubilizer in the case that solubilization is carried out. For example, the preparation of the present invention can be manufactured by a process comprising blending the drug, previously solubilized using the hydrophilic base and, if necessary, a different additive, with the hydrogel-forming polymer and, if necessary, other additives, and compression molding the resulting composition.

If required, the sustained-release preparation of the present invention may have a immediate-release portion. For example, the preparation of the present invention may be provided with such a immediate-release part by way of coating.

Depending on the intended use, the product of the invention can be provided in the form of a dry coated tablet. For example, when a high blood concentration at a definite time after administration is desired, the core tablet is manufactured according to a formulation providing for rapid drug release (with an increased amount of the drug, a reduced amount of the hydrogel-forming base, and/or an increased amount of the hydrophilic base) and, then, the outer layer is formed using a formulation providing for retarded release (with a reduced amount of the drug, an increased amount of the hydrogel-forming base and/or a reduced amount of the hydrophilic base) so that the rate of drug release may be accelerated after a predetermined time.

BEST MODE FOR WORKING THE INVENTION

The following examples are intended to describe the preparation of the present invention in further detail and should by no means be interpreted as limiting the scope of the invention.

EXAMPLE 1

| AAP | 100 (Parts by weight) |
|---|---|
| PEG6000 | 400 |
| POLYOX303 | 300 |

Acetaminophen (AAP) and PEG6000 were melted at 80° C., then cooled to solidify, and pulverized. The pulverizate and POLYOX303 were mixed in a mortar and the resulting composition was compression-molded using an oil press at a compression pressure of 1 ton/punch to provide tablets each measuring 9 mm in diameter and weighing 400 mg (AAP content: 50 mg).

Comparative Example 1

| AAP | 100 (Parts by weight) |
|---|---|
| POLYOX303 | 200 |

AAP and POLYOX303 were mixed in a mortar and the resulting mixture was compression-molded using an oil press at a compression pressure of 1 ton/punch to provide tablets each measuring 8.5 mm in diameter and weighing 300 mg (AAP content: 100 mg).

Using the tablets according to Example 1 and Comparative Example 1, the following tests were carried out.

(1) Dissolution Test 1

Figure 1:
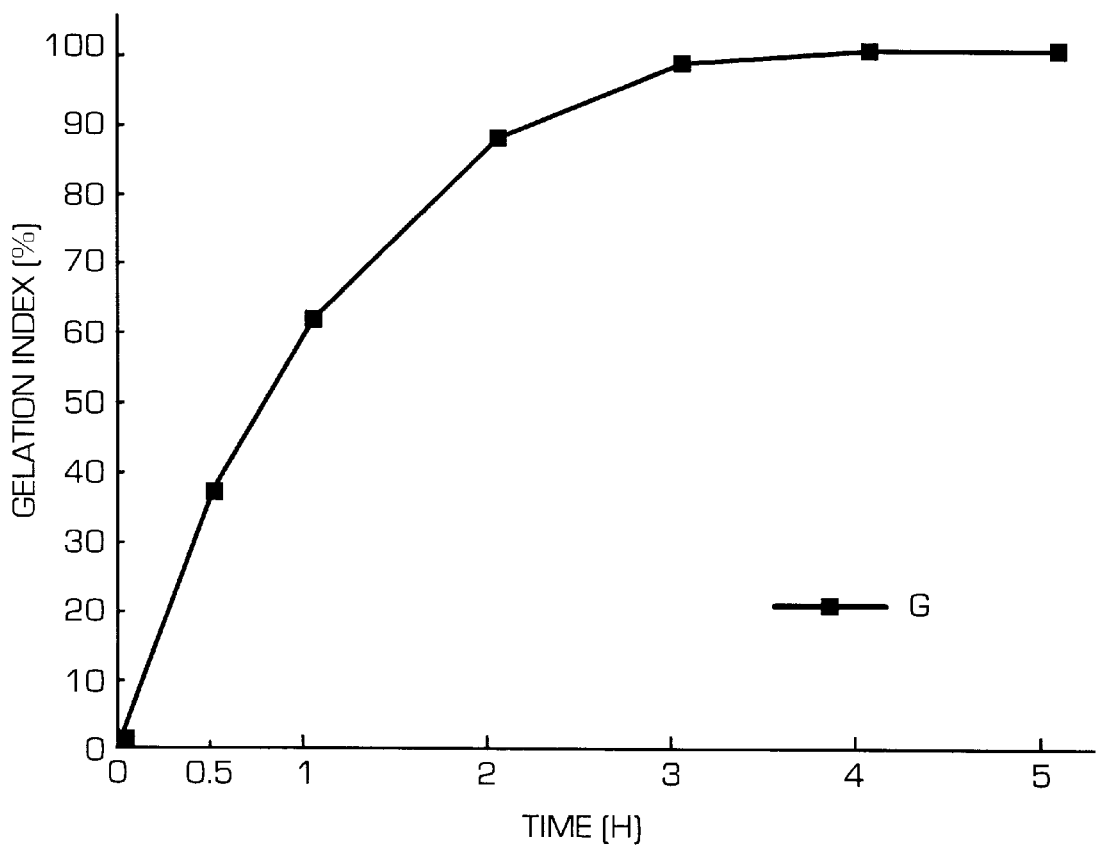
FIG. 1 shows the results of a gelation test with a PEG6000-containing hydrogel-type sustained-release preparation.
Figure 2:
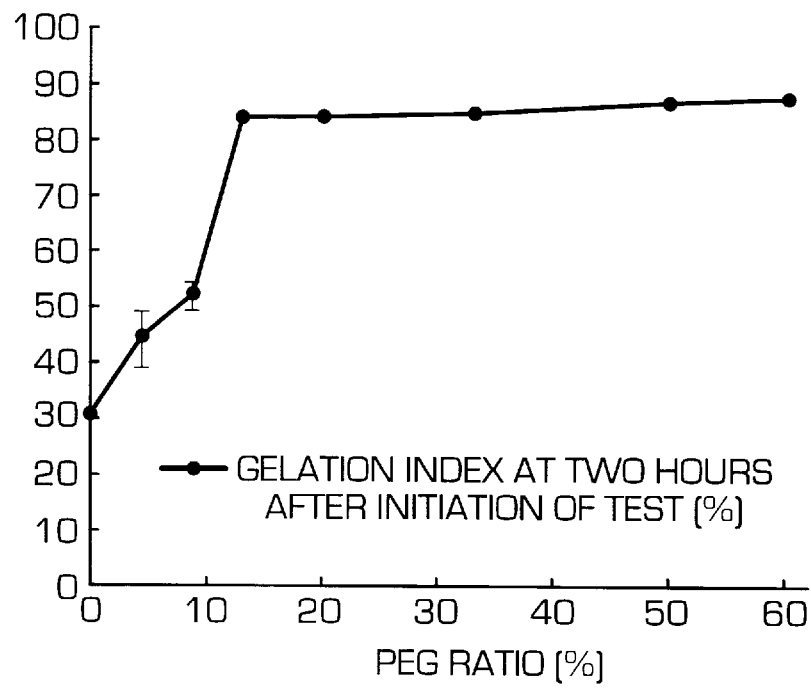
FIG. 2 shows the results of a gelation test with preparations varying in PEG6000 content.
Figure 3:
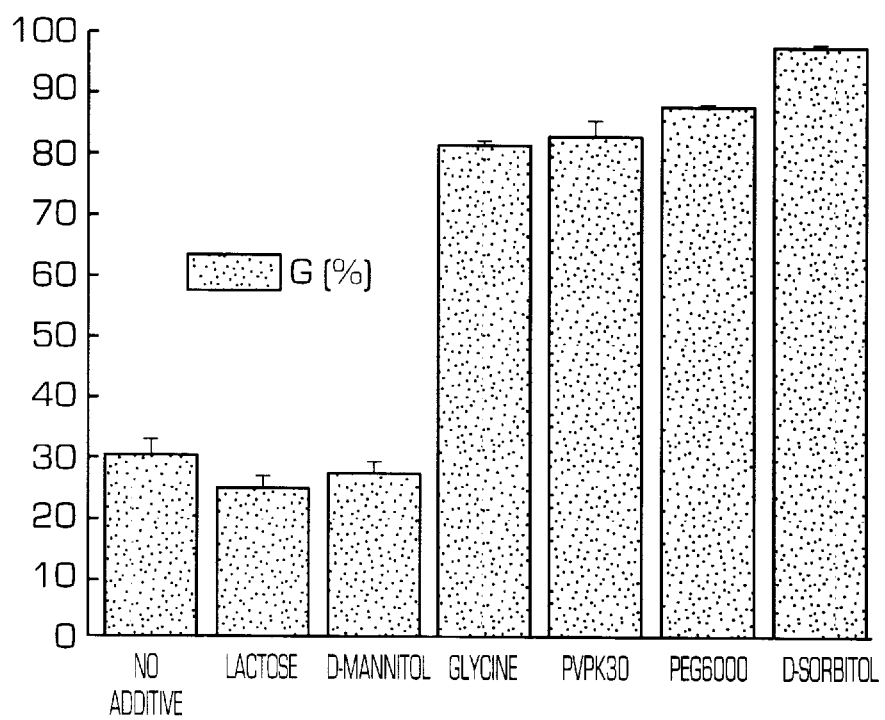
FIG. 3 shows the gelation indices of various hydrophilic bases after 2 hours.
Figure 4:
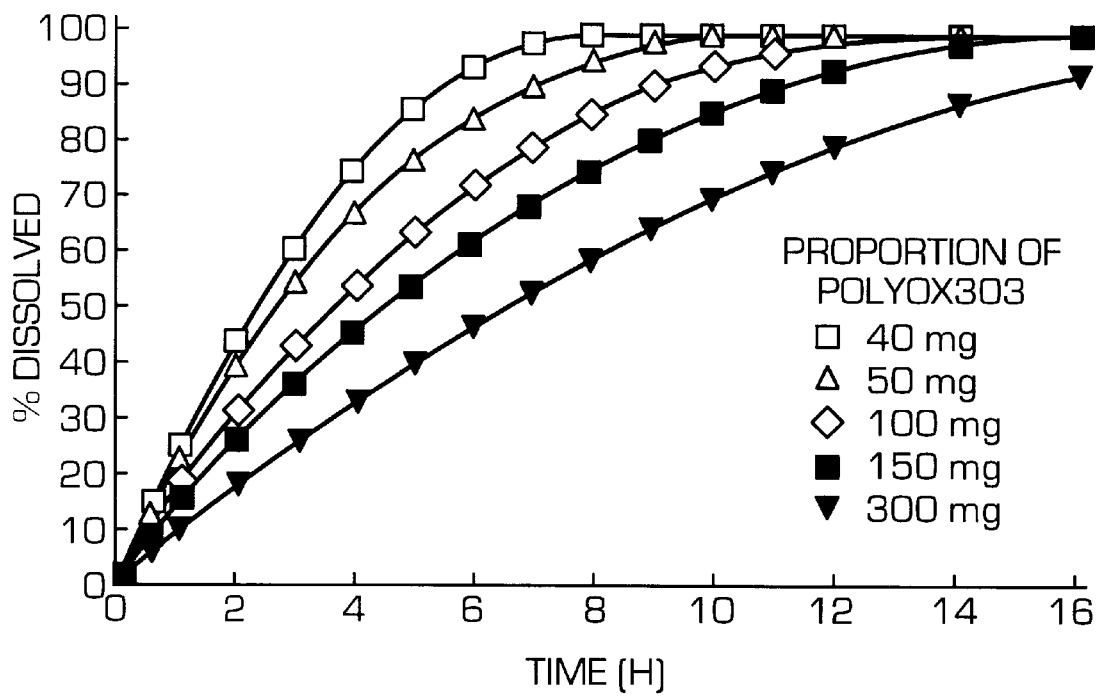
FIG. 4 shows the relationship between the amount of POLYOX303 and the pattern of release (drug: acetaminophen)
Figure 5:
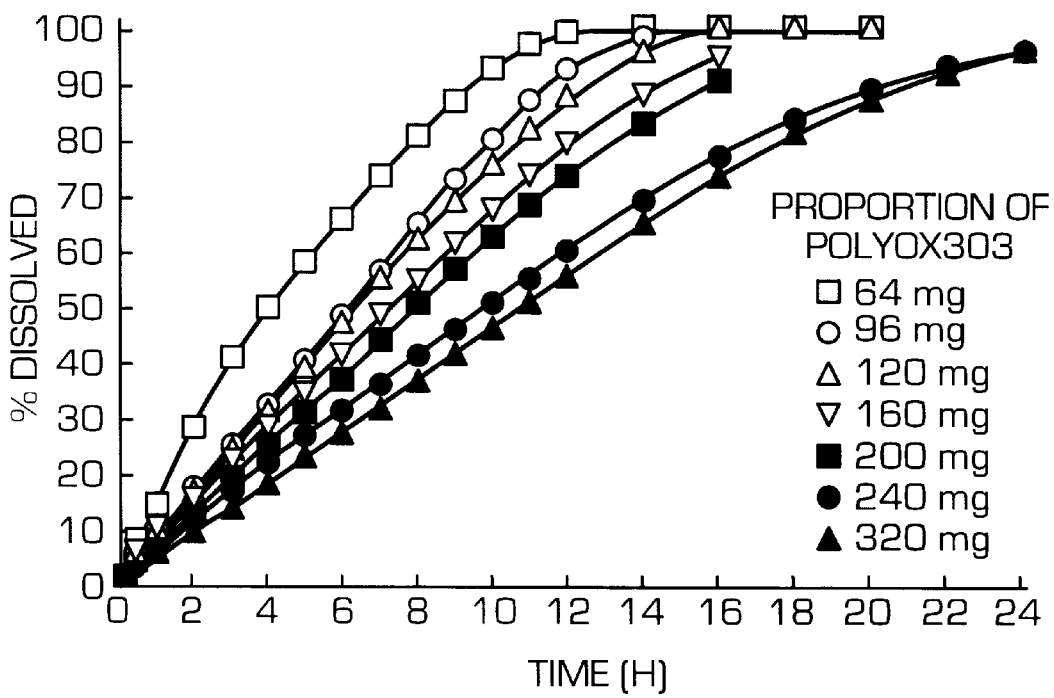
FIG. 5 shows the relationship between the amount of POLYOX303 and the pattern of release (drug: nicardipine hydrochloride)
Figure 6:
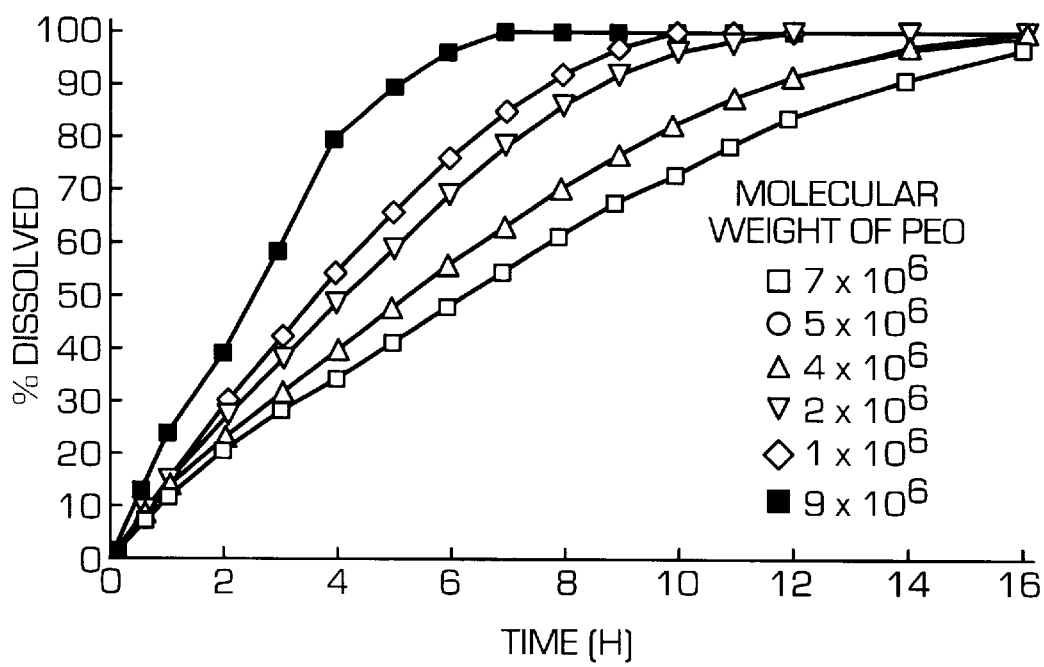
FIG. 6 shows the relationship between the molecular weight of PEO and the pattern of release (drug: acetaminophen)
Figure 7:
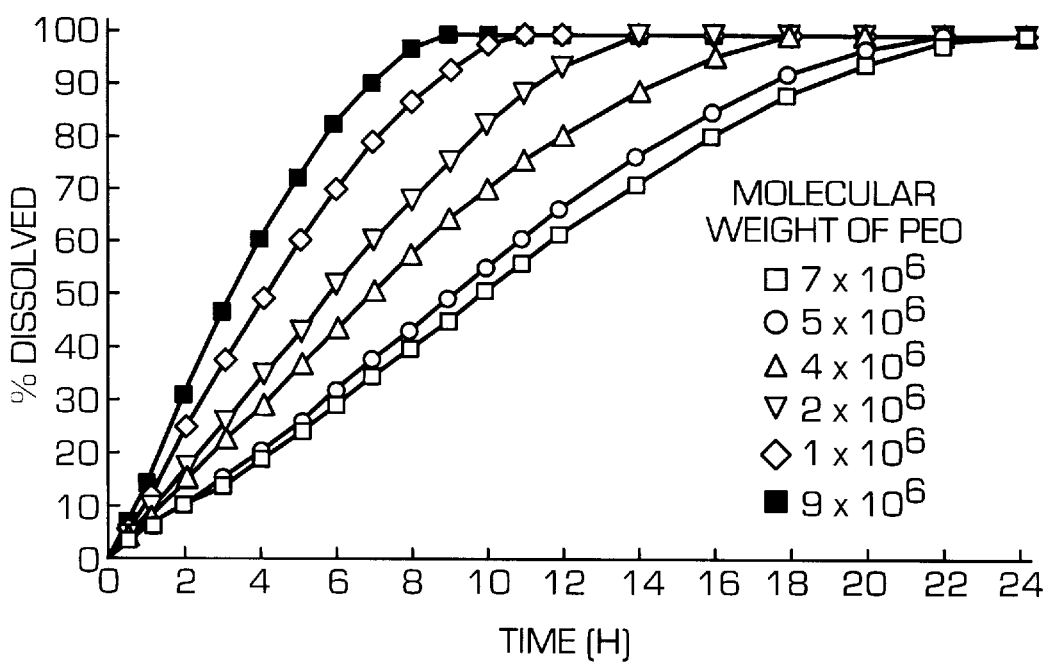
FIG. 7 shows the relationship between the molecular weight of PEO and the pattern of release (drug: nicardipine hydrochloride)
Figure 8:
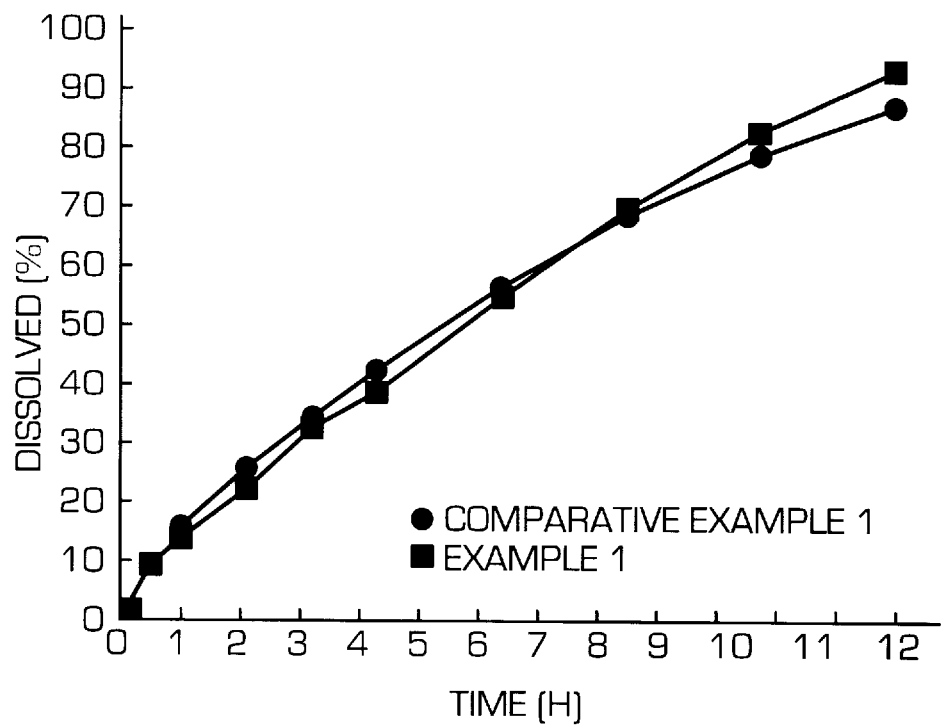
FIG. 8 shows the results of the dissolution test (paddle method) using the tablets according to Example 1 and Comparative Example 1.

Using JP Disintegration Test Fluid 2, a dissolution test was carried out by JP Dissolution Test Method 2 (paddle method). Sampling was carried out at predetermined intervals and AAP in each sample solution was assayed by the UV method (Table 9 and FIG. 8).

TABLE 9

Results of In Vitro Dissolution Test (%)
(JP Test Fluid 2, Paddle Method, 200 rpm)

| Time (h) | 0.0 | 0.5 | 1.0 | 2.0 | 3.0 | 4.0 | 6.0 | 8.0 | 10.0 | 12.0 |
|---|---|---|---|---|---|---|---|---|---|---|
| Comparative Example 1 | 0.0 | 9.4 | 15.7 | 25.8 | 34.7 | 42.8 | 56.5 | 68.3 | 78.4 | 86.4 |
| Example 1 | 0.0 | 8.8 | 13.2 | 21.8 | 32.4 | 39.1 | 55.3 | 69.2 | 81.9 | 92.1 |

(2) Gelation Test

Using JP Disintegration Test Fluid 2, a gelation test was carried out by JP Dissolution Test Method 2 (paddle method) at a paddle speed of 25 rpm. The tablets were taken out at predetermined intervals and the diameter (D obs) of the portion not forming a gel was measured, From the D obs values thus found, the gelation index (G) was calculated (Table 10 and FIG. 9)

TABLE 10

Results of Gelation Test

| Preparation | Testing Time (h) | D obs (mm) | G (%) |
|---|---|---|---|
| Comparative Example 1 | 0 | 8.5 | — |
| | 2 | 7.8 ± 0.2 | 21.5 ± 7.6 |
| | 4 | 7.5 ± 0.1 | 30.0 ± 2.5 |
| | 6 | 6.7 ± 0.1 | 50.4 ± 3.0 |
| Example 1 | 0 | 9.0 | — |
| | 2 | 5.6 ± 0.03 | 76.2 ± 0.3 |
| | 4 | 3.1 ± 0.01 | 96.0 ± 0.1 |
| | 6 | 0 ± 0.00 | 100.0 ± 0 |

(n = 3, Mean ± S.E.)

(3) Dosing Test in Dogs 1

Male beagle dogs (n=4) fasted for about 20 hours were dosed orally with the preparation of Example 1×2 tablets (AAP: 100 mg) or the preparation of Comparative Example 1 (AAP: 100 mg), together with 30 ml of water. Blood sampling was carried out at predetermined intervals and the plasma concentration of the drug was determined by the HPLC/UV method (Table 11 and FIG. 10), the absorption rate was calculated by the deconvolution method using the plasma concentration data generated by intravenous administration of 100 mg of AAP in water as the weighing function. The absorption rate at 24 hours after administration of the preparation of Example was taken as 100 (Table 12).

TABLE 11

Pharmacokinetic Parameters

| Preparation | AUC 0-24 (ng · h/ml) | C max (ng/ml) | T max (h) | MRT (h) |
|---|---|---|---|---|
| Comparative Example 1 | 1469.7 ± 537.5 | 343.7 ± 21.7 | 1.3 ± 0.3 | 4.0 ± 1.2 |
| Example 1 | 2702.8 ± 151.5 | 349.9 ± 36.1 | 1.5 ± 0.3 | 7.0 ± 0.3 |

(n = 4, Mean ± S.E.)

TABLE 12

Absorption Rate (%) after Oral Administration of Tablet to Dogs

| Time (h) | 0.0 | 0.5 | 1.0 | 2.0 | 3.0 | 4.0 | 6.0 | 8.0 | 10.0 | 12.0 | 24.0 |
|---|---|---|---|---|---|---|---|---|---|---|---|
| Comparative Example 1 | 0.0 | 8.1 | 18.7 | 27.2 | 33.3 | 37.8 | 45.9 | 50.3 | 53.1 | 55.4 | 58.8 |
| Example 1 | 0.0 | 7.5 | 14.3 | 31.0 | 39.1 | 45.9 | 60.2 | 75.5 | 87.4 | 95.6 | 100.0 |

Results

Figure 9:
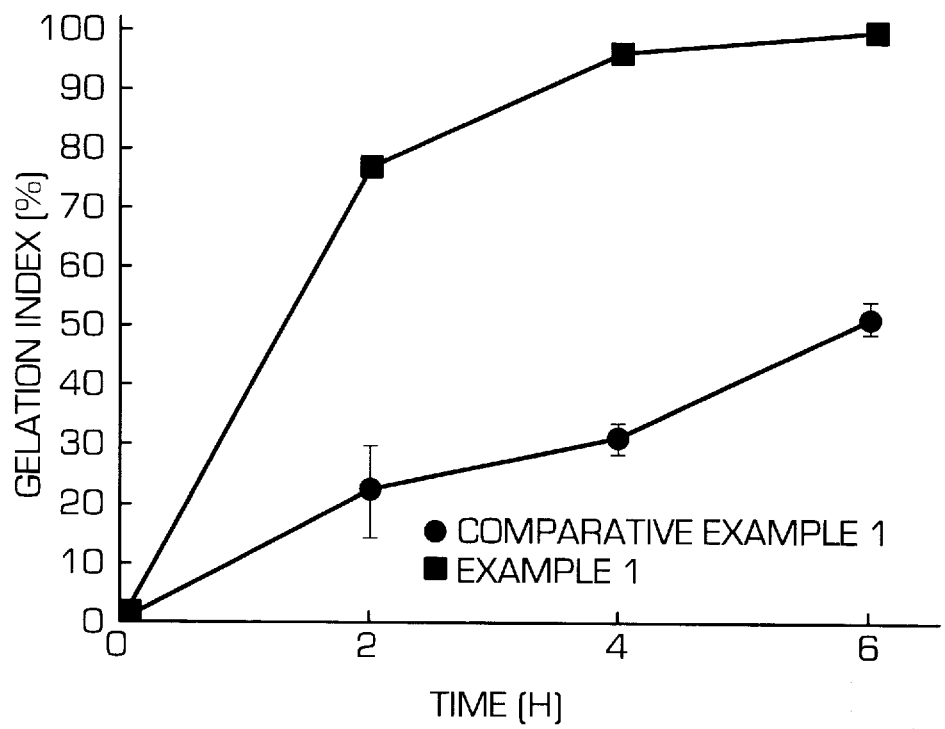
FIG. 9 shows the results of the gelation test using the tablets according to Example 1 and Comparative Example 1.
Figure 10:
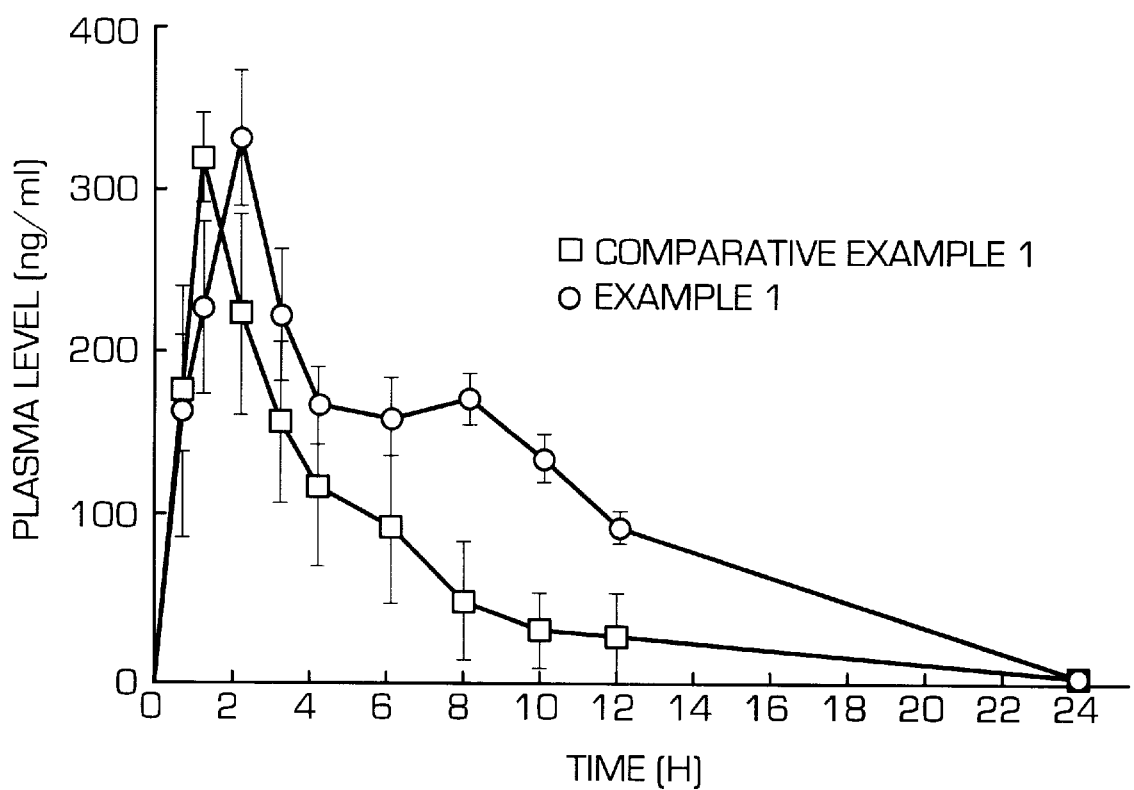
FIG. 10 shows the time courses of plasma drug concentration in dogs for the tablets according to Example 1 and Comparative Example 1.

In the in vitro dissolution test, Comparative Example 1 and Example 1 were almost identical in the pattern of dissolution (FIG. 8 and Table 9) but were markedly different from each other in water penetration rate (gelation index) (FIG. 9 and Table 10). When these preparations were administered orally to dogs, the plasma drug concentration after administration of the preparation of Example 1 was definitely well sustained as compared with the preparation of Comparative Example 1 (FIG. 10). Moreover, both the area under the plasma concentration-time curve (AUC) and the mean residence time (MRT) of the preparation of Comparative Example 1 were fairly divergent, presumably because of individual difference in transport rate in the digestive tract (Table 11). In contrast, both the AUC and MRT of the preparation of Example 1 were not much varying, suggesting that this preparation was sparingly influenced by the transport rate in the digestive tract. The absorption time was also extended, with the result that despite the substantial parity of maximum plasma concentration (C max) between the preparation of Example 1 and that of Comparative Example 1, the AUC after administration of the preparation of Example 1 was approximately 1.8 times as large.

Figure 11:
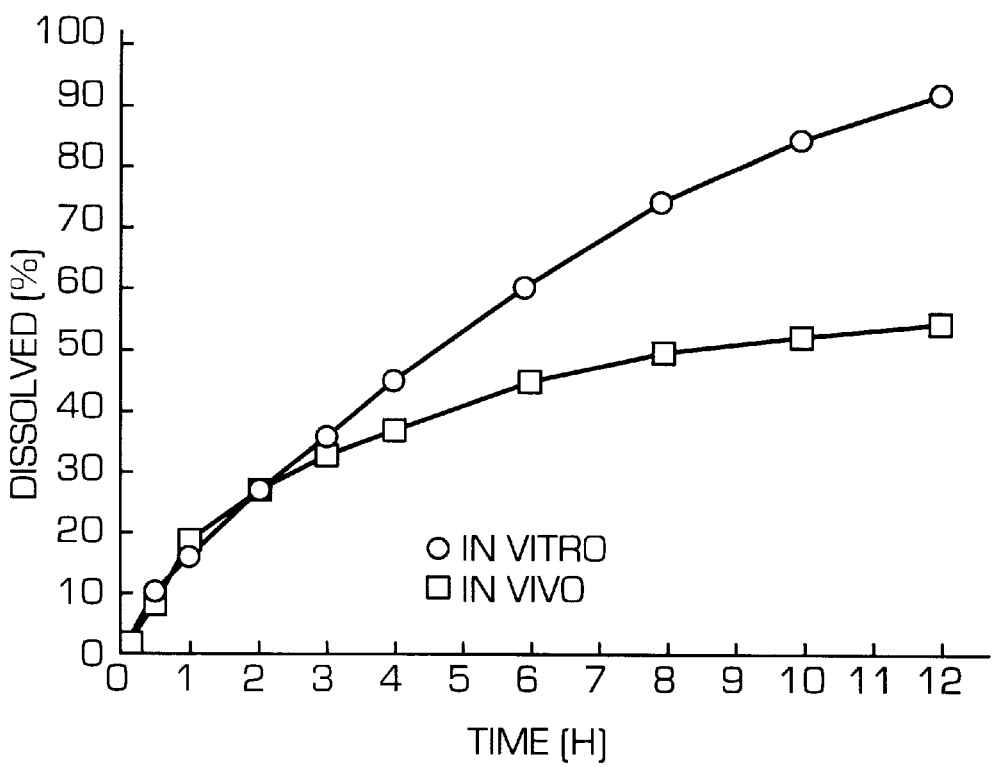
FIG. 11 shows a comparison between the dissolution test data and the absorption pattern determined by the deconvolution method for the tablet according to Comparative Example 1.
Figure 12:
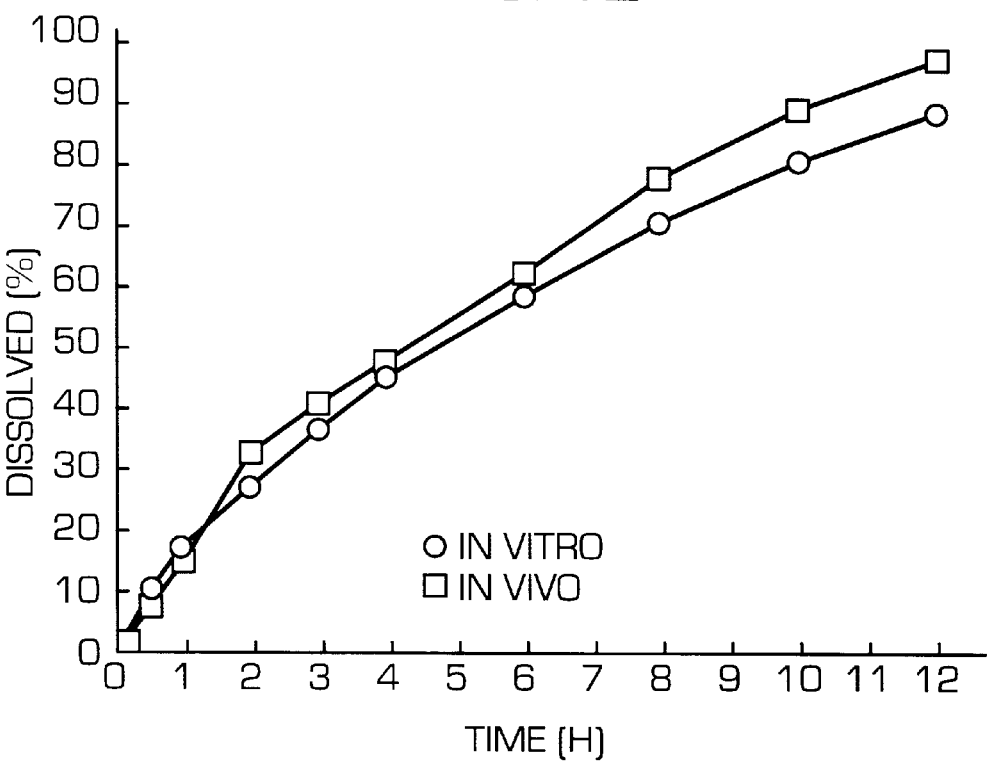
FIG. 12 shows a comparison between the dissolution test data and the absorption pattern determined by the deconvolution method for the tablet according to Example 1.

The absorption pattern determined by the deconvolution method was compared with the corresponding dissolution test data. In the case of the preparation of Comparative Example 1, the absorption of the drug during the first 2 hours after administration, when the administered, preparation was still in the upper digestive tract, was comparable to the in vitro dissolution data. However, the absorption after 2 hours was considerably decreased (FIG. 11 and Table 12). The upper digestive tract residence time of the preparation in fasted dogs is about 2 hours and it is, therefore, clear that the drug was not well released and absorbed in the lower digestive tract. In contrast, after administration of the preparation of Example 1, the pattern of absorption was comparable to the in vitro dissolution data. It is, therefore, evident that the drug was released and absorbed in the lower digestive tract as efficiently as in the upper digestive tract (FIG. 12 and Table 12).

(4) Autopsy Test in Dogs

Three male beagle dogs fasted for about 20 hours were used. Two, 4 and 6 hours before autopsy, each test preparation was administered orally together with 30 ml of water. In autopsy, the animals were bled to death under pentobarbital Na anesthesia, the abdomen was opened, and the location of the preparation in the digestive tract was determined (Table 13). The small intestine was divided into 5 segments, which were designated as Small Int. 1, 2, 3, 4 and 5, reckoning from the uppermost segment.

Results

TABLE 13

Location in Digestive Tract

| | Dog No. | 2 Hr | 4 Hr | 6 Hr |
|---|---|---|---|---|
| Comparative Example 1 | 1 | Colon | Colon | Colon |
| | 2 | Stomach | Colon | Colon |
| | 3 | Small Int. 5 | Colon | Colon |
| Example 1 | 1 | Colon | Colon | Colon |
| | 2 | Stomach | Colon | Colon |
| | 3 | Small Int. 5 | Colon | Colon |

It is clear that the preparation of Comparative Example 1, which had a low gelation index, and the preparation of Example 1, the gelation index of which had been increased by the addition of hydrophilic base, were substantially identical in the in vivo transport rate in digestive tract. At 2 hours after administration, both preparations were still in the stomach in one dog each but were already in Small Int. 5 and colon in the remaining dogs. It was, thus confirmed that the upper digestive tract residence time of the preparation was approximately 2 hours in fasted dogs in agreement with the findings heretofore reported. However, the high blood concentration after 2 hours following administration of the preparation of Example 1 indicated that the drug was released efficiently from this preparation and absorbed notwithstanding the fact that the preparation was present in the lower digestive tract.

EXAMPLE 2

| | | |
|---|---|---|
| Pd | 160 | (Parts by weight) |
| HCO-60 | 80 | |
| TC-5E | 160 | |
| PEG6000 | 400 | |
| POLYOX303 | 240 | |

Nicardipine hydrochloride (Pd), HCO-60, TC-5E and PEG6000 were dissolved in a solvent mixture (dichloromethane-methanol) and the solution was spray-dried using a spray dryer. This dry preparation was mixed with POLYOX303 in a mortar and the resulting composition was compression-molded using an oil press at a compression pressure of 1 ton/punch to provide tablets each measuring 9.0 mm in diameter and weighing 346.7 mg (Pd content: 53.3 mg).

Comparative Example 2

| Pd | 130 | (Parts by weight) |
| Tween 80 | 26 | Sustained-Release (SR) Component |
| CMEC | 130 | |
| POLYOX303 | 57.2 | |
| Pd | 30 | Immediate-Release (QR) Component |
| TC-5E | 15 | |

In a solvent mixture (dichloromethane-methanol) were dissolved nicardipine hydrochloride (Pd), Tween 80 and CM,EC and the solution was spray-dried using a spray dryer. The dried mixture was blended with POLYOX303 and the resulting composition was compression-molded using an oil press at a compression pressure of 0.8 ton/punch to provide tablets (SR) each measuring 8.0 mm in diameter and weighing 171.6 mg (Pd content: 65 mg). Separately, Pd and TC-5E were dissolved in a solvent mixture (dichloromethane-methanol) and using a Hi-Coater, this immediate-release component (QR; Pd: 15 mg) was coated on the SR (Pd: 65 mg) component to provide tablets of Comparative Example 2 each weighing 194.1 mg (Pd: 80 mg).

Using the tablets of Example 2 and Comparative Example 2, the following tests were carried out.

(1) Dissolution Test

Using JP Disintegration Test Fluid 1, a dissolution test was carried out by JP Dissolution Test Method 2 (paddle method) at a paddle speed of 200 rpm. Sampling was carried out at predetermined intervals and the Pd in each sample solution was determined by the UV method (Table 14).

TABLE 14

Results of Dissolution Test

| Time (h) | 1.0 | 2.0 | 3.0 | 4.0 | 5.0 | 6.0 | 8.0 | 10.0 | 12.0 |
|---|---|---|---|---|---|---|---|---|---|
| Comparative Example 2 (SR) | 11.9 | 29.4 | 46.4 | 61.9 | 74.4 | 82.1 | 92.1 | 97.7 | 100.0 |
| Example 2 | 14.0 | 28.7 | 45.1 | 60.5 | 73.1 | 82.2 | 94.3 | 99.8 | 99.3 |

(2) Gelation Test

Using JP Disintegration Test Fluid 1, a gelation test was carried out by JP Dissolution Test Method 2 (paddle method) at a paddle speed of 25 rpm. After a testing time of 2 hours, the tablets were taken out and the diameter (D obs) of the portion not forming a gel was measured. From the D obs value thus found, the gelation index (G) was calculated (Table 15).

TABLE 15

Results of Gelation Test

| Preparation | Testing Time (h) | D obs (mm) | G (%) |
|---|---|---|---|
| Comparative Example 2 | 0 | 8.0 | — |

TABLE 15-continued

Results of Gelation Test

| Preparation | Testing Time (h) | D obs (mm) | G (%) |
|---|---|---|---|
| (SR) | 2 | Unchanged | 0 |
| Example 2 | 0 | 9.0 | — |
| | 2 | 5.4 ± 0.02 | 76.2 ± 0.3 |

(n = 3, Mean ± S.E.)

(3) Dosage Test in Dogs

Figure 13:
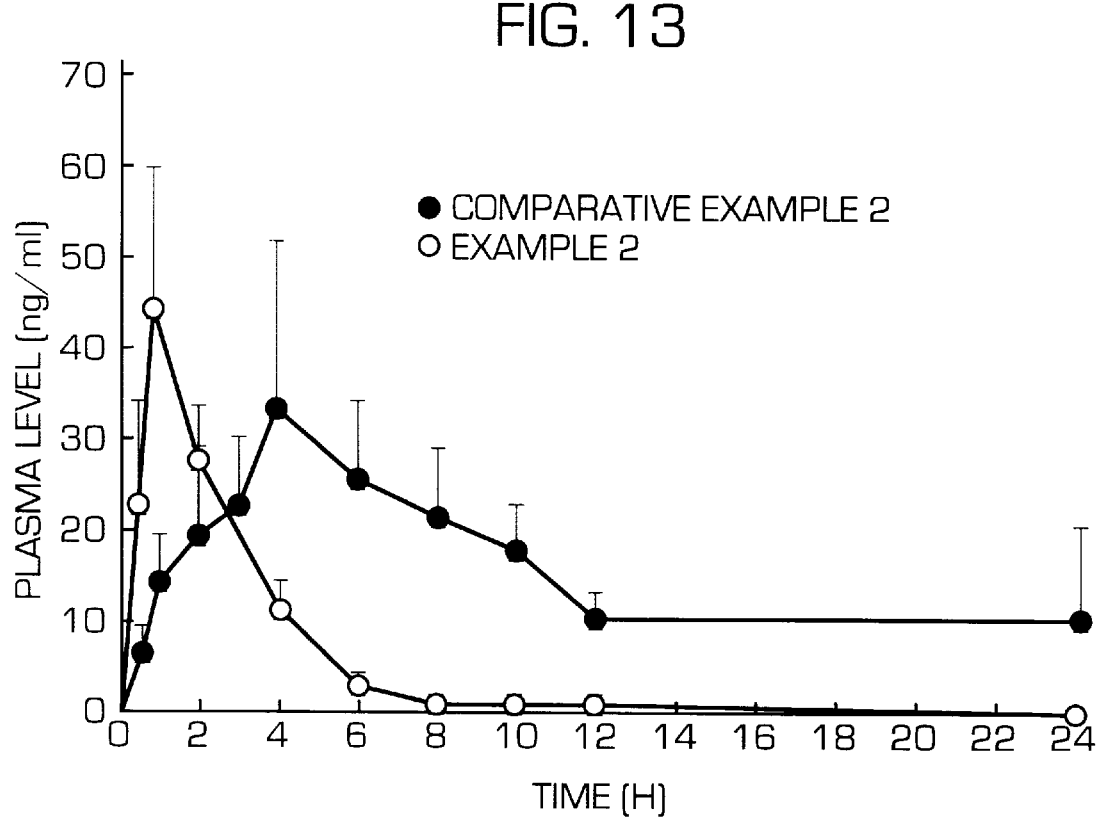
FIG. 13 shows the time courses of plasma drug concentration in dogs for the tablets according to Example 2 and Comparative Example 2.

Male beagle dogs (n=6) fasted for about 20 hours were orally dosed with the preparation of Example 2×3 tablets, (Pd: 160 mg) or the preparation of Comparative Example 2×2 tablets (Pd: 160 mg), together with 30 ml of water. Blood sampling was performed at predetermined intervals and the plasma concentration of the drug was determined by the HPLC/UV method (Table 16 and FIG. 13).

TABLE 16

Pharmacokinetic Parameters

| Preparation | AUC (ng · h/ml) | C max (ng/ml) | T max (h) |
|---|---|---|---|
| Example 2 (Pd: 160 mg) | 375.7 ± 89.3 | 52.9 ± 15.5 | 7.3 ± 3.5 |
| Comparative Example 2 (Pd: 160 mg) | 125.0 ± 31.8 | 53.6 ± 12.5 | 1.3 ± 0.2 |

(n = 6, Mean ± S.E.)

Results

In the in vitro dissolution test, the preparation of Comparative Example 2 (SR) and that of Example 2 were substantially identical in the pattern of dissolution (Table 14) but differed from each other significantly in the rate of water penetration (gelation index) (Table 15). When these preparations were orally administered to dogs, the preparation of Example 2 showed a definitely sustained plasma drug concentration as compared with the preparation of Comparative Example 2. With respect to the preparation of Comparative Example 2, the plasma concentration of the drug decreased significantly after 2 hours when the administered preparation entered into the lower digestive tract, indicating that the drug was hardly released or absorbed in the lower digestive tract. In contrast, in the case that the preparation of Example 2 was administered, the plasma concentration was well maintained even after 2 hours when the preparation was moved into the lower digestive tract, indicating that the drug was effectively released and absorbed in the lower digestive tract. Furthermore, although the preparation of Example 2 showed a C max value comparable to that following administration of the preparation of Comparative Example 2, the former preparation gave an AUC value approximately 3-fold as large due to the prolonged absorption period.

EXAMPLE 3

| Example 3 | | | |
|---|---|---|---|
| Pd | 65 | (Parts by weight) | Sustained-Release (SR) Component |
| Tween 80 | 13 | | |
| CMEC | 65 | | |
| PEG6000 | 65 | | |
| POLYOX303 | 65 | | |
| Pd | 15 | | Immediate-Release (QR) Component |

Nicardipine hydrochloride (Pd), Tween 80 and CMEC were dissolved in a solvent mixture (dichloromethane-methanol) and the solution was spray-dried using a spray dryer. The dried mixture was blended with PEG6000 and POLYOX303 and the resulting composition was compression-molded using an oil press at a compression pressure of 1.0 ton/punch to provide tablets (SR) each measuring 8.5 mm in diameter and weighing 273 mg (QR; Pd content: 65 mg). For use as the immediate-release (QR) component, tablets each containing 15 mg of Pd were separately prepared.

Comparative Example 3

| Comparative Example 3 | | | |
|---|---|---|---|
| Pd | 65 | (Parts by weight) | Sustained-Release (SR) Component |
| Tween 80 | 13 | | |
| CMEC | 65 | | |
| POLYOX303 | 28.6 | | |
| Pd | 15 | | Immediate-Release (QR) Component |
| TC-5E | 7.5 | | |

Nicardipine hydrochloride (Pd), Tween 80 and CMEC were dissolved in a solvent mixture (dichloromethane-methanol) and the solution was spray-dried using a spray dryer. The dried mixture was blended with POLYOX303 and the resulting composition was compression-molded using an oil press at a compression pressure of 0.8 ton/punch to provide tablets (SR) each measuring 8.0 mm in diameter and weighing 171.6 mg (Pd content: 65 mg). Separately, Pd and TC-5E were dissolved in a solvent mixture (dichloromethane-methanol) and using a Hi-Coater, this immediate-release component (QR; Pd content: 15 mg) was coated on the SR component (Pd content: 65 mg) to provide tablets each weighing 194.1 mg (Pd: 80 mg).

(1) Dissolution Test

Using JP Disintegration Test Fluid 2, a dissolution test was carried out by JP Dissolution Test Method 2 (paddle method) at a paddle speed of 200 rpm. Sampling was carried out at predetermined intervals and Pd in each sample solution was assayed by the UV method.

Figure 14:
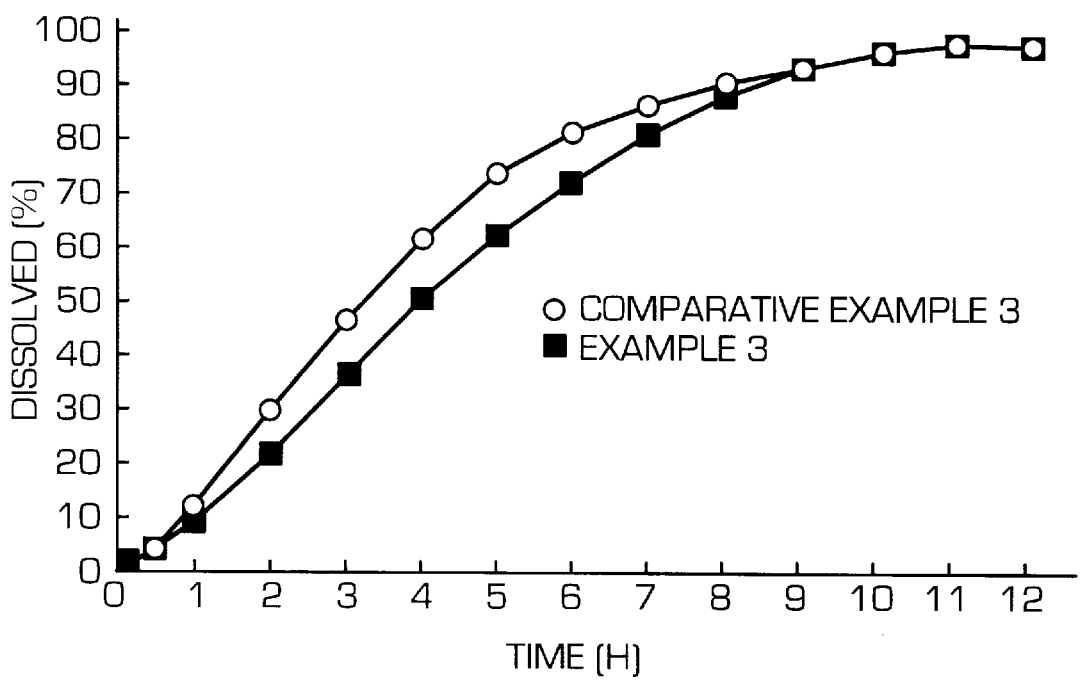
FIG. 14 shows the results of the dissolution test (paddle method) using the tablets according to Example 3 (SR) and Comparative Example 3 (SR)

The results of the above dissolution test using the preparation of Comparative Example 3 (SR) and that of Example 3 (SR) are shown in FIG. 14.

(2) Gelation Test

Using JP Disintegration Test Fluid 1, a dissolution test was carried out by JP Dissolution Test Method 2 (paddle method) at a paddle speed of 25 rpm. After 2 hours, the tablets were taken out, the gel layer was removed and the weight (W obs) of the portion not forming a gel was determined. From the W obs value, the gelation index (G) was calculated by means of Equation 2 given below (Table 17).

TABLE 17

Results of Gelation Test (n = 3, Mean ± S.E.)

| Preparation | Testing Time (h) | W obs (g) | G (%) |
|---|---|---|---|
| Comparative Example 3 (SR) | 0 | 0.167 | — |
| | 2 | 0.153 ± 0.0 | 8.2 ± 1.4 |
| Example 3 (SR) | 0 | 0.276 | — |
| | 2 | 0.055 ± 0.4 | 79.6 ± 0.4 |

Equation 2

$$G(\%) = \left(1 - \frac{(W\ obs)}{(W\ ini)}\right) \times 100$$

Figure 15:
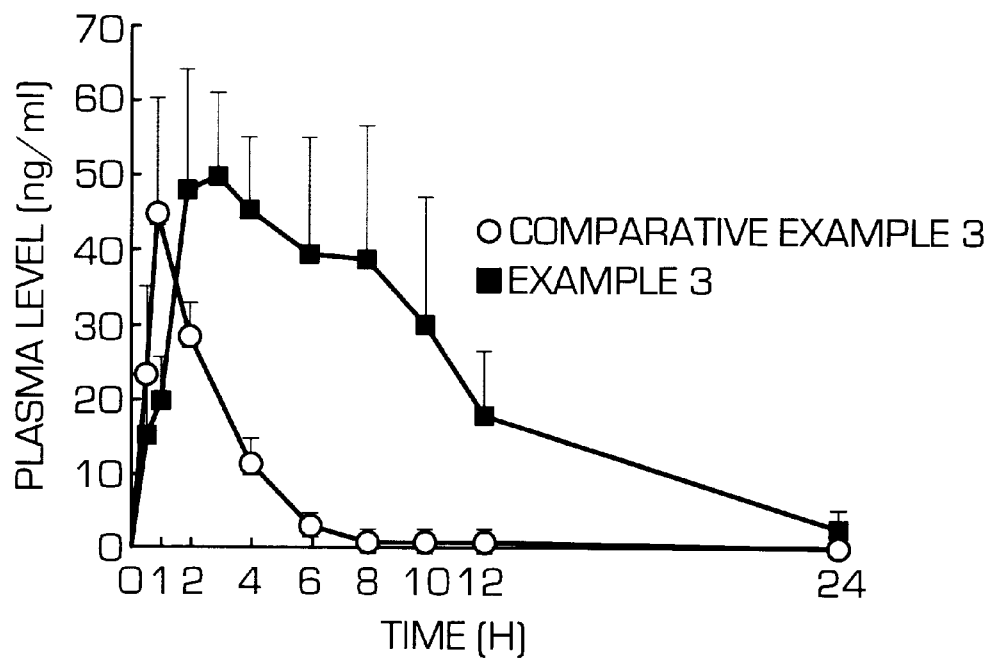
FIG. 15 shows the time courses of plasma drug concentration in dogs for the tablets according to Example 3 and Comparative Example 3.

W obs: The residual weight after removal of the gel layer after initiation of test W ini: The weight of the tablet before initiation of test (3) Dosage Test in Dogs Male beagle dogs (n =6) fasted for about 20 hours were orally dosed with two tablets each of the preparation of Example 3 SR and QR (Pd: 160 mg) or 2 tablets of the preparation of Comparative Example 3 (Pd: 160 mg), together with 30 ml of water. Blood sampling was performed at predetermined intervals and the plasma concentration of the drug was determined by the HPLC/UV method (FIG. 15 and Table 18).

TABLE 18

Pharmacokinetic Parameters (n = 6, Mean ± S.E.)

| Preparation | AUC 0–24 (ng · h/ml) | C max (ng/ml) | T max (h) | MRT (h) |
|---|---|---|---|---|
| Comparative Example 3 | 125.0 ± 31.8 | 53.6 ± 12.5 | 1.3 ± 0.2 | 2.4 ± 0.4 |
| Example 3 | 547.1 ± 180.4 | 81.6 ± 14.8 | 3.9 ± 1.1 | 6.3 ± 1.0 |

(4) Autopsy Test in Dogs

Three male beagle dogs fasted for about 20 hours were used. Two, 4 and 6 hours before autopsy, each test preparation was administered orally together with 30 ml of water. In autopsy, the animals were bled to death under pentobarbital Na anesthesia, the abdomen was opened, and the location of the tablet in the digestive tract was determined (Table 19). The small intestine was divided into 5 segments, which were designated as Small Int. 1, 2, 3, 4 and 5, reckoning from the uppermost segment.

TABLE 19

Location in Digestive Tract
(Small Intestine was Divided into 5 Segments)

| | Dog No. | 2 Hr | 4 Hr | 6 Hr |
|---|---|---|---|---|
| Comparative Example 3 | 4 | Colon | Colon | Colon |
| | 5 | Colon | Colon | Colon |
| | 6 | Small Int. 1 | Colon | Colon |
| Example 3 | 4 | Small Int. 5 | Colon | Colon |
| | 5 | Colon | Colon | Colon |

TABLE 19-continued

Location in Digestive Tract
(Small Intestine was Divided into 5 Segments)

| Dog No. | 2 Hr | 4 Hr | 6 Hr |
|---|---|---|---|
| 6 | Small Int. 1 | Colon | Colon |

Results

In the in vitro dissolution test, the preparation of Comparative Example 3 (SR) and that of Example 3 (SR) were substantially identical in the pattern of dissolution (Table 14) but diddered considerably from each other in the gelation index (Table 17). Autopsy revealed substantially the same transport rate in the digestive tract for the preparation of Example 3 and that of Comparative Example 3 (Table 19). When these prepartaions were administered orally to dogs, the time course of plasma drug concentration after administration of the preparation of Example 3 was definitely better sustained as compared with the preparation of Comparative Example 3. With respect to the preparation of Comparative Example 3, the plasma concentration decreased remarkably after 2 hours when the administered preparation was moved into the lower digestive tract, indicating that the drug was hardly released and absorbed in the lower digestive tract. In contrast, with respect to the preparation of Example 3, the plasma drug concentration was well sustained even after 2 hours when the administered preparation was moved into the lower digestive tract, indicating that the drug was effectively released and absorbed even in the lower digestive tract (FIG. 15). Moreover, although the C max after administration of the preparation of Example 3 was not much different from that after administration of the preparation of Comparative Example 3, the former preparation gave an AUC value about 4.4 times as large due to the prolonged absorption period (Table 18).

EXAMPLE 4

| Example 4 | |
|---|---|
| Pd | 80 (mg) |
| PVP K30 | 32 |
| HCO-60 | 16 |
| POLYOX303 | 240 |
| Lubricant | 4 |

Nicardipine hydrochloride (Pd), PVP K30 and HCO-60 were dissolved in methanol. Using a fluidized-bed granulator, this solution was sprayed over POLYOX303 to provide granules. To the granules was added the lubricant and the resulting composition was mixed and then compression-molded to provide tablets each measuring 9.5 mm in diameter and weighing 372 mg (Pd content: 80 mg).

EXAMPLE 5

| Example 5 | |
|---|---|
| Pd | 80 (mg) |
| TC-5E | 32 |
| HCO-60 | 16 |
| PEG6000 | 32 |
| POLYOX303 | 240 |
| Lubricant | 8 |
| Fluidizer | 4 |

Nicardipine hydrochloride (Pd), TC-5E and HCO-60 were dissolved in water-methanol (1:9) and the solution was spray-dried. To the dried mixture were added POLYOX303 and 4 mg equivalent of lubricant and the mixture was dry-granulated. To the granules were added 4 mg equivalent of lubricant as well as fluidizer and the resulting composition was mixed and compression-molded to provide tablets each measuring 9.5 mm in diameter and weighing 412 mg (Pd content: 80 mg).

EXAMPLE 6

| Example 6 | |
|---|---|
| Pd | 80 (mg) |
| TC-5E | 32 |
| HCO-60 | 32 |
| PEG6000 | 32 |
| POLYOX303 | 384 |
| Lubricant | 11.2 |
| Fluidizer | 5.6 |

Nicardipine hydrochloride (Pd), TC-5E, HCO-60 and PEG6000 were dissolved in water-methanol (1:9) and the solution was spray-dried. To this dried preparation were added POLYOX303 and 5.6 mg equivalent of lubricant and the mixture was dry-granulated. To the granules thus prepared were added 5.6 mg equivalent of lubricant as well as fluidizer and the resulting composition was mixed and compression-molded to provide tablets each measuring 11 mm in diameter and weighing 576.8 mg (Pd content: 80 mg).

EXAMPLE 7

| Example 7 | |
|---|---|
| Pd | 80 (mg) |
| TC-5E | 64 |
| Tween 80 | 32 |
| PEG6000 | 32 |
| POLYOX303 | 360 |
| Lubricant | 11.4 |
| Fluidizer | 5.7 |

Nicardipine hydrochloride (Pd), TC-5E and Tween 80 were dissolved in water-methanol (1:9) and the solution was spray-dried. To this dried preparation were added PEG6000, POLYOX303 and 5.7 mg equivalent of the lubricant and the mixture was dry-granulated. To the granules thus prepared were added 5.7 mg of lubricant as well as fluidizer and the resulting composition was mixed and compression-molded to provide tablets each measuring 11 mm in diameter and weighing 585.1 mg (Pd content: 80 mg).

EXAMPLE 8

Pd and TC-5E were dissolved in water-methanol (1:9) and using a Hi-Coater, the immediate-release component (Pd: 20 mg) was coated on the tablets of Example 7 (Pd: 80 mg) to provide tablets each weighing 625.1 mg (Pd: 100 mg).

EXAMPLE 9

Pd and HPC-SL were dissolved in methanol and using a Hi-Coater, the immediate-release component (Pd: 20 mg) was coated on the tablets of Example 7 (Pd: 80 mg) to provide tablets each weighing 625.1 mg (Pd: 100 mg).

EXAMPLE 10

| Example 10 | |
|---|---|
| Pd | 80 (mg) |
| TC-5E | 64 |
| HCO-40 | 32 |
| PEG6000 | 48 |
| POLYOX303 | 344 |
| Lubricant | 11.4 |
| Fluidizer | 5.7 |

Pd, TC-5E and HCO-40 were dissolved in water-methanol (1:9) and the solution was spray-dried. To this dried preparation were added PEG6000, POLYOX303 and 5.7 mg equivalent of lubricant and the mixture was dry-granulated. To the granules thus prepared were added 5.7 mg equivalent of lubricant as well as fluidizer and the resulting composition was mixed and compression-molded to provide tablets each measuring 11 mm in diameter and weighing 585.1 mg (Pd content: 80 mg).

EXAMPLE 11

| Example 11 | |
|---|---|
| Pd | 100 (mg) |
| TC-5E | 80 |
| HCO-40 | 40 |
| PEG6000 | 48 |
| POLYOX303 | 300 |
| Lubricant | 11.4 |
| Fluidizer | 5.7 |

Pd, TC-5E and HCO-40 were dissolved in water-methanol (1:9) and the solution was spray-dried. To this dried preparation were added PEG6000, POLYOX303 and 5.7 mg equivalent of lubricant and the mixture was dry-granulated. To the granules were added 5.7 mg equivalent of lubricant as well as fluidizer and the resulting composition was mixed and compression-molded to provide tablets each measuring 11 mm in diameter and weighing 585.1 mg (Pd content: 100 mg).

(1) Dissolution Test

Using JP Disintegration Test Fluid 1, a dissolution test was carried out by JP Dissolution Test Method 2 (paddle method) at a paddle speed of 200 rpm. Sampling was carried out at predetermined intervals and Pd in each sample solution was assayed by the UV method.

Figure 16:
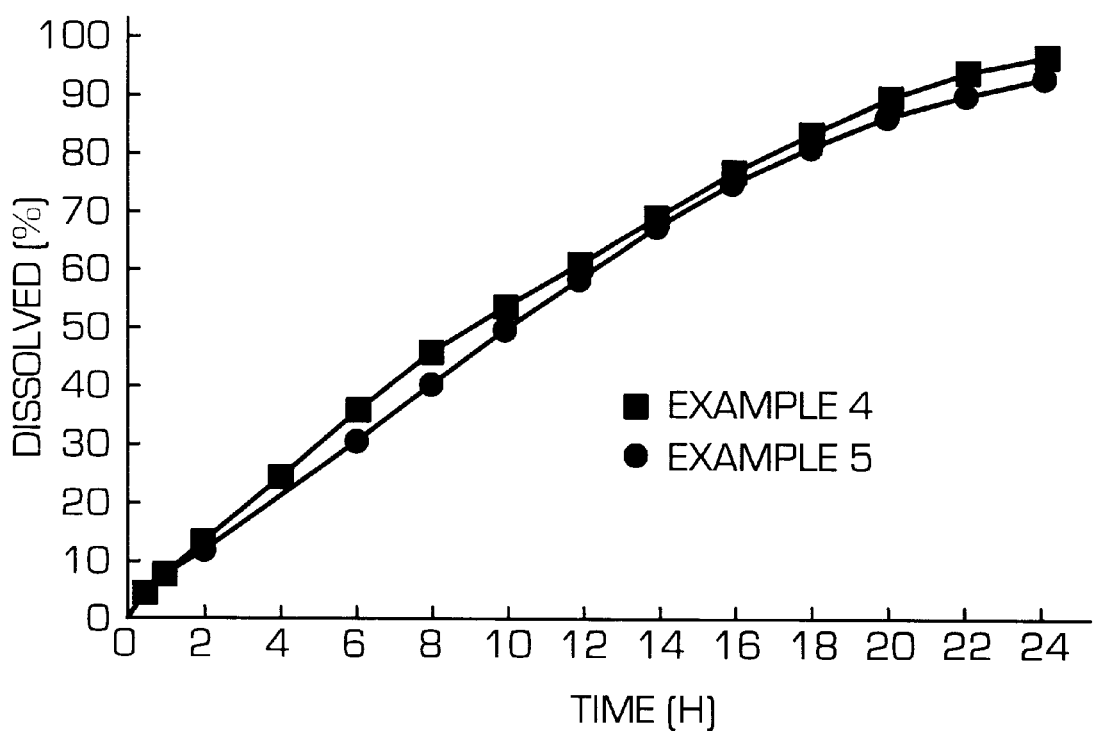
FIG. 16 shows the results of the dissolution test (paddle method) using the tablets according to Examples 4 and 5.

The results of dissolution tests for preparations of Examples 4 and 5 are shown in FIG. 16.

Figure 17:
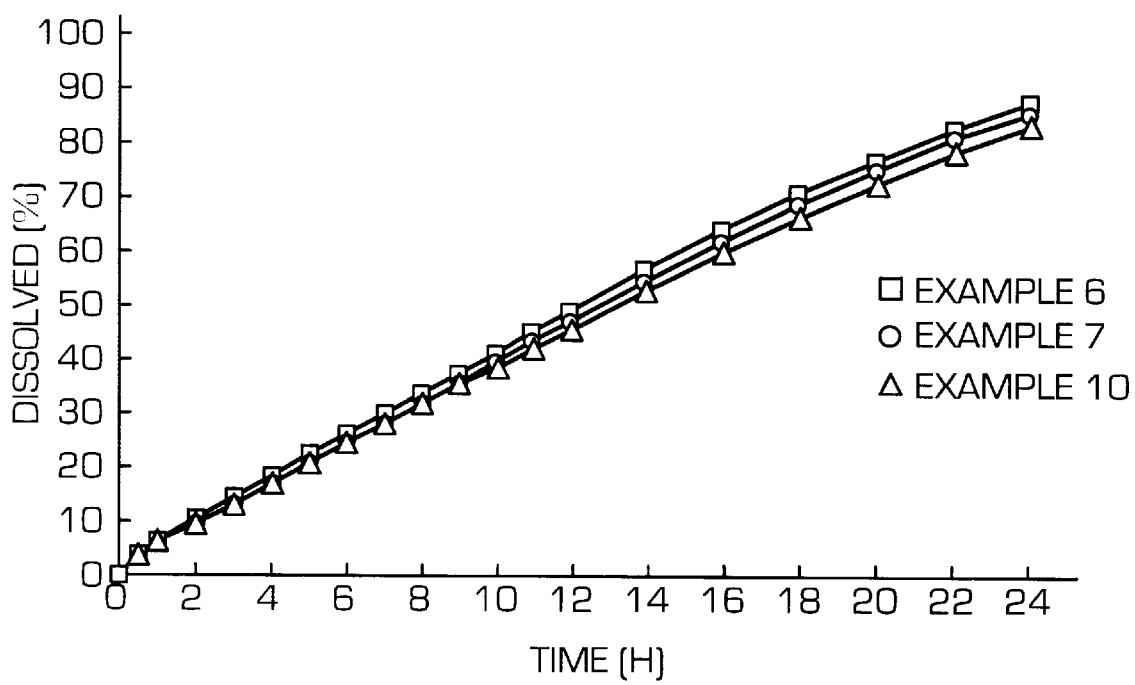
FIG. 17 shows the results of the dissolution test (paddle method) using the tablets according to Examples 6, 7 and 10.

The results of dissolution tests for preparations of Example 6, Example 7 and Example 10 are shown in FIG. 17.

(2) Dosage Test in Dogs

Male beagle dogs (n=6) were orally dosed with 2 tablets of the preparation of Example 5 or 2 tablets of the preparation of Example 6 once a day for 4 consecutive days. Blood sampling was carried out at predetermined intervals and the plasma concentration of the drug was determined by the HPLC/UV method.

Results

Both of the preparations of Examples 5 and 6, in a once-a-day administration, showed high $C_{24}$ hr values (blood concentrations at 24 hours after administration) and high bioavailabilities.

EXAMPLE 12

| Example 12 | |
|---|---|
| DF | 37.5 (mg) |
| PEG6000 | 37.5 |
| POLYOX303 | 75.0 |

Diclofenac Na (DF), PEG6000 and POLYOX303 were mixed in a mortar and using an oil press the composition was compression-molded at a compression pressure of 1 ton/punch to provide tables measuring 7 mm in diameter and weighing 150 mg (DF: 37.5 mg).

Comparative Example 4

| Comparative Example 4 | |
|---|---|
| DF | 37.5 (mg) |
| POLYOX303 | 75.0 |

DF and POLYOX303 were mixed in a mortar and using an oil press the mixture was compression-molded at a compression pressure of 1 ton/punch to provide tablets each measuring 6.0 mm in diameter and weighing 112.5 mg (DF content: 37.5 mg).

(1) Dissolution Test

Figure 18:
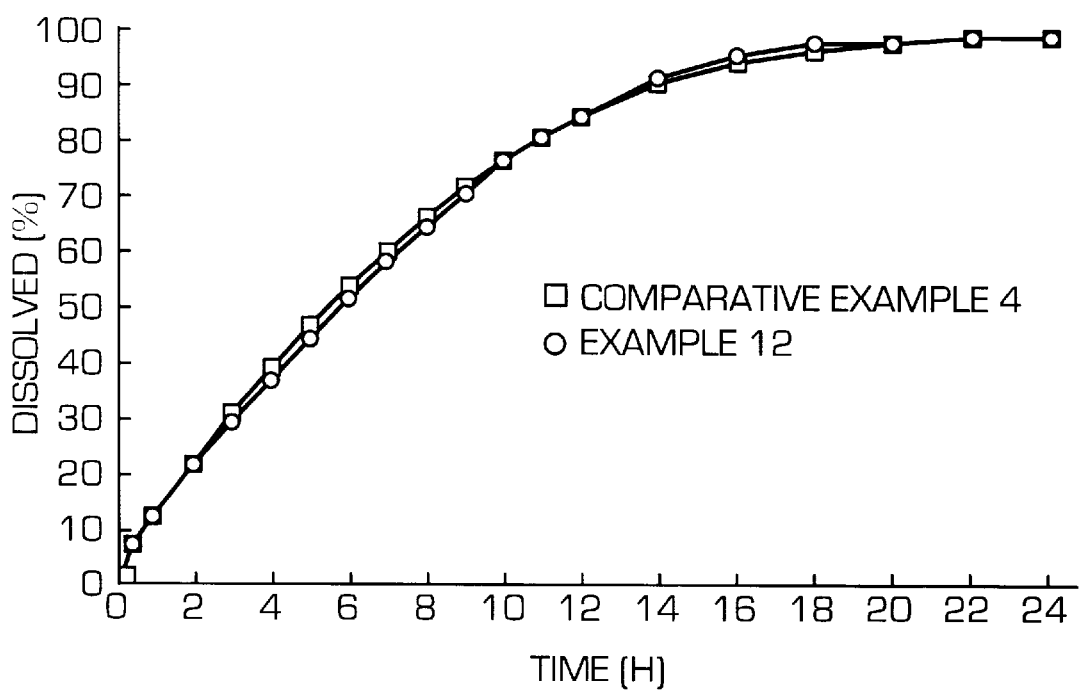
FIG. 18 shows the results of the dissolution test (paddle method) using the tablets according to Example 12 and Comparative Example 4.

Using JP Disintegration Test Fluid 2, a dissolution test was carried out by JP Dissolution Test Method 2 (paddle method). Sampling was carried out at predetermined intervals and DF in each sample solution was assayed by the UV method (FIG. 18).

(2) Gelation Test

Using JP Disintegration Test Fluid 2, a gelation test was carried out by JP Dissolution Test Method 2 (paddle method) at a paddle speed of 25 rpm. The tablets were taken out at 2 hours intervals and the diameter (D obs) of the portion not forming a gel was measured. From the D obs value thus found, the gelation index (G) was calculated (Table 20).

TABLE 20

Results of Gelation Test (n = 3, Mean ± S.E.)

| Preparation | Testing Time (h) | G (%) |
|---|---|---|
| Example 12 | 2 | 88.2 ± 1.1 |
| Comparative Example 4 | 2 | 37.0 ± 4.6 |

(3) Dosage Test in Dogs

Male beagle dogs (n=5) fasted for about 20 hours were orally dosed with the preparation of Example 12 (DF: 37.5 mg) or the preparation of Comparative Example 4 (DF: 37.5 mg), together with 30 ml of water. Blood sampling was carried out at predetermined intervals and the plasma concentration of the drug was determined by the HPLC/UV method (Table 21 and FIG. 19).

TABLE 21

Oral Dosage Test (in Fasting Condition)

| Preparation | AUC 0–12 (ng · h/ml) | C max (ng/ml) | T max (h) |
|---|---|---|---|
| Comparative Example 4 | 5052 ± 1357 | 1188 ± 147 | 1.7 ± 0.6 |
| Example 12 | 8537 ± 1941 | 1381 ± 222 | 3.0 ± 1.3 |

(n = 5, Mean ± S.E.)

Results

Figure 19:
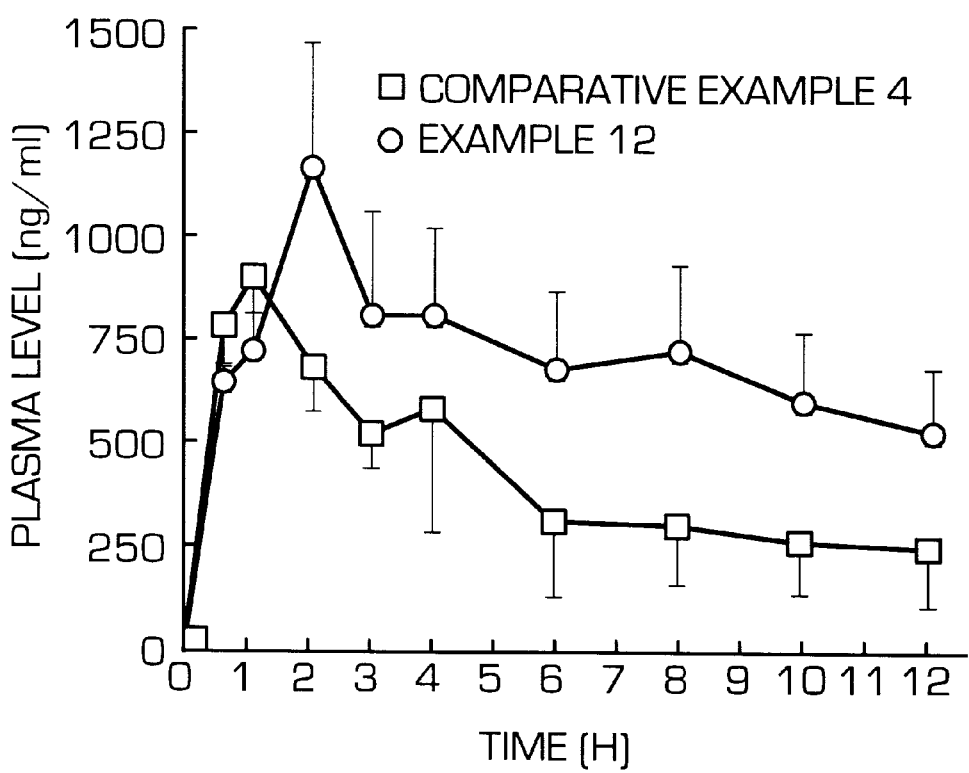
FIG. 19 shows the time courses of plasma drug concentration in dogs for the tablets according to Example 12 and Comparative Example 4.

In the in vitro dissolution test, the preparation of Example 12 and that of Comparative Example 4 were substantially identical in the pattern of dissolution (FIG. 18) but differed considerably from each other in the rate of water penetration (gelation index) (Table 20). When these preparations were administered orally to dogs, the preparation of Example 12 showed a definitely prolonged blood concentration as compared with the preparation of Comparative Example 4 (FIG. 19). Furthermore, in comparison with Comparative Example 4, Example 12 gave an AUC value which was about 1.7 times as large (Table 21). Thus, even for diclofenac Na which is an acidic drug, it was confirmed that the application of the present invention resulted in an efficient release and absorption of the drug in the lower digestive tract as well.

EXAMPLE 13

| Example 13 | |
|---|---|
| DF | 75 (mg) |
| PEG6000 | 75 |
| POLYOX303 | 150 |

Diclofenac Na (DF), PEG6000 and POLYOX303 were mixed in a mortar and using an oil press the composition was compression-molded at a compression pressure of 1 ton/punch to provide tablets each measuring 8.5 mm in diameter and weighing 300 mg (DF content: 75 mg).

EXAMPLE 14

| Example 14 | |
|---|---|
| DF | 75 (mg) |
| PEG6000 | 75 |
| POLYOX303 | 300 |

Diclofenac Na (DF), PEG6000 and POLYOX303 were mixed in a mortar and using an oil press the composition was compression-molded at a compression pressure of 1 ton/punch to provide tablets each measuring 9.5 mm in diameter and weighing 450 mg (DF content: 75 mg).

EXAMPLE 15

| Example 15 | |
|---|---|
| Famotidine | 40 (mg) |
| PEG6000 | 30 |
| POLYOX303 | 150 |
| Lubricant | 2 |

Famotidine, PEG6000, POLYOX303 and lubricant were mixed and compression-molded to provide tablets each measuring 8.0 mm in diameter and weighing 222 mg (famotidine content: 40 mg).

EXAMPLE 16

| Example 16 | |
|---|---|
| Barnidipine Hydrochloride | 15 (mg) |
| TC-5E | 30 |
| HCO-40 | 5 |
| PEG20000 | 40 |
| POLYOX303 | 207 |
| Lubricant | 3 |

Barnidipine hydrochloride, TC-5E and HCO-40 were dissolved in water-methanol (1:9). Separately, PEG20000 and POLYOX303 were mixed. Using a fluidized-bed granulator, the latter mixture was sprayed with the above solution. The granules thus prepared were dried, and after addition of lubricant, the composition was compression-molded to provide tablets each measuring 9.0 mm in diameter and 300 mg (barnidipine HCl content: 15 mg).

EXAMPLE 17

| Example 17 | |
|---|---|
| Amosulalol Hydrochloride | 40 (mg) |
| Pluronic F68 | 40 |
| POLYOX303 | 196 |
| Lubricant | 4 |

Amosulalol hydrochloride, Pluronic F68, POLYOX303 and lubricant were mixed, pulverized and dry-granulated. The granules were then compression-molded to provide tablets each measuring 8.5 mm in diameter and weighing 280 mg (amosulalol HCl content: 40 mg).

EXAMPLE 18

| Example 18 | |
|---|---|
| Tamusulosin Hydrochloride | 0.2 (mg) |
| D-Sorbitol | 17.8 |
| Polyox WSR N-60K | 180 |
| Lubricant | 2 |

Tamusulosin hydrochloride, D-sorbitol and PEO (Polyox WSR N-60K) were wet-granulated with ethanol and dried. To this dried granules was added lubricant and the resulting composition was mixed and then compression-molded to provide tablets each measuring 8 mm in diameter and weighing 200 mg (tamusulosin HCl content: 0.2 mg).

EXAMPLE 19

| Example 19 | |
|---|---|
| Indeloxazine Hydrochloride | 60 (mg) |
| Sucrose | 37 |
| HPMC (90SH30000) | 180 |
| Lubricant | 3 |

Indeloxazine hydrochloride, sucrose, HPMC and lubricant were mixed and dry-granulated. The granules were then compression-molded to provide tablets each measuring 9 mm in diameter and 280 mg (indeloxazine HCl content: 60 mg).

EXAMPLE 20

| Example 20 | |
|---|---|
| Formoterol Fumarate | 0.16 (mg) |
| Anhydrous Maltose | 47.84 |
| Carbopol 940 | 100 |
| Lubricant | 2 |

Formoterol fumarate, anhydrous maltose, Carbopol 940 and lubricant were mixed and the resulting composition was compression-molded to provide tablets each measuring 7 mm in diameter and weighing 150 mg (formoterol fumarate content: 0.2 mg).

EXAMPLE 21

| Example 21 | |
|---|---|
| AAP | 100 (mg) |
| PEG6000 | 200 |
| PEO (Polyox WSR N-60K) | 300 |

Acetaminophen (AAP), PEG6000 and PEO (Polyox WSR N-60K, mean molecular weight: 200 million) were mixed in a mortar and using an oil press the mixture was compression-molded at a pressure of 1 ton/punch to provide tablets each measuring 11 mm in diameter and weighing 600 mg (AAP content: 100 mg).

Comparative Example 5

| Comparative Example 5 | |
|---|---|
| AAP | 100 (mg) |
| PEO (Polyox WSR N-60K) | 300 |

AAP and PEO (POLYOX WSR N-60K) were mixed in a mortar and using an oil press the mixture was compression-molded at a pressure of 1 ton/punch to provide tables each measuring 9 mm in diameter and weighing 400 mg (AAP content: 100 mg).

(1) Dissolution Test

Using JP Disintegration Test Fluid 2, a dissolution test was carried out by JP Dissolution Test Method 2 (paddle method) at a paddle speed of 200 rpm. Sampling was carried out at predetermined intervals and AAP in each sample solution was assayed by the UV method.

(2) Gelation Test

Using JP Disintegration Test Fluid 2, a gelation test was carried out by JP Dissolution Test Method 2 (paddle method) at a paddle speed of 25 rpm. After 2 hours, the tablets were taken out and the diameter (D obs) of the portion not forming a gel was measured. From the D obs value thus found, the gelation index (G) was calculated.

(3) Dosage Test in Dogs

Male beagle dogs (n =6) fasted for about 20 hours were orally dosed with the preparation of Comparative Example 5 (AAP: 100 mg) or the preparation of Example 20 (AAP: 100 mg), together with 30 ml of water. Blood sampling was carried out at predetermined intervals and the plasma concentration of the drug was determined by the HPLC/UV method.

Results

In the in vitro dissolution test, the preparation of Comparative Example 5 and that of Example 20 were substantially identical in the pattern of dissolution but the preparation of Example 20, which contained a hydrophilic base, showed a gelation index greater than that of the preparation of Comparative Example 5. When these preparations were respectively administered orally to dogs, the plasma concentration of the drug was definitely better sustained in the case of Example 21 as compared with Comparative Example 5. The maximum plasma concentration (C max) of the drug after administration of the preparation of Example 21 was substantially equal to that after administration of the preparation of Comparative Example 5 but the former preparation was superior in AUC and MRT. Moreover, after administration of the preparation of Example 21, the blood concentration of the drug was sustained at a high level up to 12 hours.

INDUSTRIAL APPLICABILITY

The preparation of the present invention absorbs water to undergo substantially complete gelation during its stay in the upper digestive tract and moves down into the lower digestive tract undergoing constant erosion and continues to release the drug on further erosion. Therefore, this preparation provides for a favorable sustained release of the drug even in the colon which is low in water content to insure drug release lasting for about 6 to 18 hours (about 12 to 24 hours if the release in the upper digestive tract is taken into account) and, hence, insures a steady drug concentration in the blood.

Since the conventional sustained-release preparations release drugs only in the upper digestive tract, the duration of release is about 6 hours at most and subsequent maintenance of blood concentration is relied on the biological half-life inherent to the drug. In contrast, with respect to the preparation of the present invention, the duration of drug release per se is increased. Accordingly, even when the drug is that having a short biological half-life and the sustained release thereof has heretofore been considered difficult, a sufficient blood concentration can be maintained over a time period of more than 12 hours.

Thus, the preparation of the present invention is capable of sustaining the efficacy of the drug and the number of administration can be reduced. Further, the side effect of the drug can be reduced by suppressing rapid increase of blood concentration of the drug and the constant blood concentration of the drug can be maintained.

As demonstrated in the examples described above, the present invention is capable of prolonging the absorption of various types of drugs such as acetaminophen, which is a neutral drug, nicardipine hydrochloride, which is a basic drug, and diclofenac Na, which is an acidic drug. Therefore, the present invention provides a pharmaceutical technology having a great versatility without depending on physical properties of drugs.

What is claimed is:

1. A method for providing drug-release not only in the upper digestive tract including stomach and small intestine but also in the lower digestive tract including the colon, comprising the steps of:
    (A) orally administering a preparation having a gelation index of 70% or more, said preparation comprising:
    (1) a drug, wherein the amount of said drug is not more than 85% by weight based on the total preparation,
    (2) an additive which has a solubility such that the volume of water required for dissolving 1 gram of said additive is not more than 5 ml, wherein the amount of said additive is from 5 to 80% by weight based on the total preparation, and
    (3) a hydrogel-forming polymer having a viscosity of not less than 1000 cps as measured at 1% concentration in water at 25° C., wherein the amount of said hydrogel-forming polymer is from 10 to 95% by weight based on the total preparation and not less than 70 mg per one preparation;
    (B) substantially complete gelling of the preparation in the upper digestive tract including stomach and small intestine;
    (C) through travelling in gel-form to the lower digestive tract, releasing the drug not only in the upper digestive tract including stomach and small intestine but also in the lower digestive tract including the colon.

2. The method as claimed in claim 1, wherein said preparation has a gelation index of 80% or more.

3. The method as claimed in claim 1, wherein said additive has a solubility such that the volume of water required for dissolving 1 gram of said additive is not more than 4 ml.

4. The method as claimed in claim 1, wherein the amount of said drug is not more than 80% by weight based on the total preparation.

5. The method as claimed in claim 1, wherein the amount of said additive is from 5 to 60% by weight based on the total preparation.

6. The method as claimed in claim 1, wherein the amount of said hydrogel-forming polymer is from 10 to 90% by weight based on the total preparation.

7. The method as claimed in claim 1, wherein the amount of said drug is not more than 80% by weight based on the total preparation, the amount of said additive is from 5 to 60% by weight based on the total preparation, and the amount of said hydrogel-forming polymer is from 10 to 90% by weight based on the total preparation.

8. The method as claimed in claim 1, wherein the amount of said hydrogel-forming polymer is not less than 100 mg per one preparation.

9. The method as claimed in claim 1, wherein said drug is nicardipine hydrochloride.

10. The method as claimed in claim 1, wherein said drug is tamusulosin hydrochloride.

11. The method as claimed in claim 1, wherein said additive is selected from the group consisting of a highly hydrophilic polymer, a sugar alcohol, a sugar, a surfactant, a salt, an organic acid, an amino acid and an amino sugar.

12. The method as claimed in claim 11, wherein said additive is selected from the group consisting of polyethylene glycol, polyvinylpyrrolidone, D-sorbitol, xylitol, sucrose, anhydrous maltose, D-fructose, dextran, polyoxyethylene-hydrogenated castor oil, polyoxyethylene-polyoxypropylene glycol, polyoxyethylene-sorbitan higher fatty acid ester, sodium chloride, magnesium chloride, citric acid, tartaric acid, glycine, β-alanine, lysine hydrochloride and meglumine.

13. The method as claimed in claim 12, wherein said additive is selected from the group consisting of polyethylene glycol, polyvinylpyrrolidone, and D-sorbitol.

14. The method as claimed in claim 1, wherein said additive is polyethylene glycol.

15. The method as claimed in claim 1, wherein said additive is selected from the group consisting of polyethylene oxide, hydroxypropylmethylcellulose sodium carboxymethylcellulose, hydroxyethylcellulose and carboxyvinyl polymers.

16. The method as claimed in claim 15, wherein said hydrogel-forming polymer is polyethylene oxide.

17. The method as claimed in claim 1, wherein said additive is polyethylene glycol and said hydrogel-forming polymer is polyethylene oxide.

18. The method as claimed in claim 1, wherein drug-release is provided in the upper digestive tract and also in the lower digestive tract including the colon.

19. The method as claimed in claim 1, wherein said preparation is a tablet.

20. The method as claimed in claim 1, wherein said gelation index is defined by the equation $$(1-(D\ obs)^3/(D\ ini)^3) \times 100$$

wherein (D ini) is the diameter of the preparation before testing and (D obs) is the diameter of the preparation not gelled at two hours after beginning the test.

21. The method as claimed in claim 1, wherein said gelation index is defined by the equation $$(1-(W\ obs)/(W\ ini)) \times 100$$

wherein (W ini) is the weight of the preparation before testing and (W obs) is the weight of the preparation not gelled at two hours after beginning the test.

22. A method for providing drug-release not only in the upper digestive tract including stomach and small intestine but also in the lower digestive tract including the colon, comprising the steps of:
    (A) orally administering a preparation having a gelation index of 70% or more, said preparation comprising:
    (1) a drug, wherein the amount of said drug is not more than 85% by weight based on the total preparation,
    (2) an additive which has a solubility such that the volume of water required for dissolving 1 gram of said additive is not more than 5 ml, wherein the amount of said additive is from 5 to 80% by weight based on the total preparation, and
    (3) a hydrogel-forming polymer having a viscosity of not less than 1000 cps as measured at 1% concentration in water at 25° C., wherein the amount of said hydrogel-forming polymer is from 10 to 95% by weight based on the total preparation and not less than 70 mg per one preparation; and
    (B) absorbing water before the preparation is in the low-water lower digestive tract including the colon.

23. A method for delivering a gel to the lower digestive tract including the colon for drug-release, comprising the steps of:
(A) orally administering a preparation having a gelation index of 70% or more, said preparation comprising:
(1) a drug, wherein the amount of said drug is not more than 85% by weight based on the total preparation,
(2) an additive which has a solubility such that the volume of water required for dissolving 1 gram of said additive is not more than 5 ml, wherein the amount of said additive is from 5 to 80% by weight based on the total preparation, and
(3) a hydrogel-forming polymer having a viscosity of not less than 1000 cps as measured at 1% concentration in water at 25° C., wherein the amount of said hydrogel-forming polymer is from 10 to 95% by weight based on the total preparation and not less than 70 mg per one preparation;
(B) substantially complete gelling in the upper digestive tract including stomach and small intestine; and
(C) releasing the drug not only in the upper digestive tract including stomach and small intestine but also in the lower digestive tract including the colon.

24. A method for maintaining a steady blood level of a drug, comprising the steps of:
(A) orally administering a preparation having a gelation index of 70% or more, said preparation comprising:
(1) a drug, wherein the amount of said drug is not more than 85% by weight based on the total preparation,
(2) an additive which has a solubility such that the volume of water required for dissolving 1 gram of said additive is not more than 5 ml, wherein the amount of said additive is from 5 to 80% by weight based on the total preparation, and
(3) a hydrogel-forming polymer having a viscosity of not less than 1000 cps as measured at 1% concentration in water at 25° C., wherein the amount of said hydrogel-forming polymer is from 10 to 95% by weight based on the total preparation and not less than 70 mg per one preparation;
(B) substantially complete gelling in the upper digestive tract including stomach and small intestine; and
(C) releasing the drug not only in the upper digestive tract including stomach and small intestine but also in the lower digestive tract including the colon.

25. A method for maintaining a steady blood level of a drug, comprising the steps of:
(A) solubilizing a drug to provide a preparation having a gelation index of 70% or more, said solubilizing comprising combining the drug, in an amount not more than 85% by weight based on the total preparation, with
(i) an additive which has a solubility such that the volume of water required for dissolving 1 gram of said additive is not more than 5 ml, wherein the amount of said additive is from 5 to 80% by weight based on the total preparation, and
(ii) a hydrogel-forming polymer having a viscosity of not less than 1000 cps as measured at 1% concentration in water at 25° C., wherein the amount of said hydrogel-forming polymer is from 10 to 95% by weight based on the total preparation and not less than 70 mg per one preparation;
(B) orally administering the solubilized drug preparation of step (A); and
(C) substantially complete gelling in the upper digestive tract including stomach and small intestine; followed by drug-release in the lower digestive tract including the colon.

26. The method of claim 1, wherein the method comprises oral administration to a human and the substantially complete gelation is about 4 to 5 hours after administration.

27. The method of claim 26, wherein the method comprises a portion of the preparation having undergone gelation still remaining in the colon 6 hours after administration.

28. The method of claim 27, wherein the method comprises a portion of the preparation having undergone gelation still remaining in the colon 8 hours after administration.

29. The method of claim 27, wherein the method comprises a portion of the preparation having undergone gelation still remaining in the colon 12 hours after administration.

30. A method for providing drug-release not only in the upper digestive tract including stomach and small intestine but also in the lower digestive tract including the colon, comprising the steps of:
(A) orally administering a preparation having a gelation index of 70% or more, said preparation comprising:
(1) a drug, wherein the amount of said drug is not more than 85% by weight based on the total preparation,
(2) an additive which has a solubility such that the volume of water required for dissolving 1 gram of said additive is not more than 5 ml, wherein the amount of said additive is from 5 to 80% by weight based on the total preparation, and
(3) a hydrogel-forming polymer, wherein the amount of said hydrogel-forming polymer is from 10 to 95% by weight based on the total preparation;
(B) substantially complete gelling of the preparation in the upper digestive tract including stomach and small intestine;
(C) through travelling in gel-form to the lower digestive tract, releasing the drug not only in the upper digestive tract including stomach and small intestine but also in the lower digestive tract including the colon.

* * * * *